United States Patent
Refaeli et al.

(10) Patent No.: US 10,864,259 B2
(45) Date of Patent: Dec. 15, 2020

(54) METHODS AND COMPOSITIONS FOR THE TREATMENT OF MELANOMA

(71) Applicant: TAIGA BIOTECHNOLOGIES, INC., Aurora, CO (US)

(72) Inventors: Yosef Refaeli, Denver, CO (US); Brian C. Turner, Denver, CO (US); Gregory Alan Bird, Littleton, CO (US)

(73) Assignee: TAIGA BIOTECHNOLOGIES, INC., Aurora, CO (US)

( * ) Notice: Subject to any disclaimer, the term of this patent is extended or adjusted under 35 U.S.C. 154(b) by 0 days.

(21) Appl. No.: 16/184,086

(22) Filed: Nov. 8, 2018

(65) Prior Publication Data

US 2019/0060434 A1 Feb. 28, 2019

Related U.S. Application Data

(62) Division of application No. 15/668,451, filed on Aug. 3, 2017, now Pat. No. 10,149,898.

(51) Int. Cl.
*A61K 39/39* (2006.01)
*A61K 39/00* (2006.01)
*C12N 5/0783* (2010.01)

(52) U.S. Cl.
CPC .. *A61K 39/001152* (2018.08); *A61K 39/0011* (2013.01); *A61K 39/39* (2013.01); *C12N 5/0638* (2013.01); *A61K 2039/515* (2013.01); *C12N 2501/606* (2013.01); *C12N 2510/00* (2013.01)

(58) Field of Classification Search
CPC ... A61K 39/0011; A61K 39/39; C12N 5/0638
USPC .................................................... 424/93.71
See application file for complete search history.

(56) References Cited

U.S. PATENT DOCUMENTS

| | | |
|---|---|---|
| 4,900,322 A | 2/1990 | Adams |
| 4,963,489 A | 10/1990 | Naughton et al. |
| 5,289,858 A | 3/1994 | Grabenkort |
| 5,476,996 A | 12/1995 | Wilson et al. |
| 5,652,122 A | 7/1997 | Frankel et al. |
| 5,670,617 A | 9/1997 | Frankel et al. |
| 5,674,980 A | 10/1997 | Frankel et al. |
| 5,698,767 A | 12/1997 | Wilson et al. |
| 5,747,641 A | 5/1998 | Frankel et al. |
| 5,804,604 A | 9/1998 | Frankel et al. |
| 5,811,301 A | 9/1998 | Cameron |
| 5,824,837 A | 10/1998 | Chen et al. |
| 5,843,728 A | 12/1998 | Seed et al. |
| 5,847,082 A | 12/1998 | Rother et al. |
| 5,849,288 A | 12/1998 | Reisner |
| 5,851,828 A | 12/1998 | Seed et al. |
| 5,912,170 A | 6/1999 | Seed et al. |
| 6,004,811 A | 12/1999 | Seed et al. |
| 6,040,177 A | 3/2000 | Riddell et al. |
| 6,284,240 B1 | 9/2001 | Seed et al. |
| 6,358,739 B1 | 3/2002 | Baetge et al. |
| 6,392,013 B1 | 5/2002 | Seed et al. |
| 6,410,014 B1 | 6/2002 | Seed et al. |
| 6,451,558 B1 | 9/2002 | Cooke et al. |
| 6,451,601 B1 | 9/2002 | Baetge et al. |
| 6,645,501 B2 | 11/2003 | Dowdy |
| 6,753,162 B1 | 6/2004 | Seed et al. |
| 7,135,287 B1 | 11/2006 | Lonberg et al. |
| 7,311,920 B1 | 12/2007 | Devico et al. |
| 7,582,745 B2 | 9/2009 | Sah et al. |
| 7,767,453 B2 | 8/2010 | Zhang |
| 8,034,334 B2 | 10/2011 | Dudley et al. |
| 8,211,422 B2 | 7/2012 | Eshhar et al. |
| 8,481,492 B2 | 7/2013 | Edenhofer et al. |
| 8,637,307 B2 | 1/2014 | June et al. |
| 8,697,854 B2 | 4/2014 | Schendel et al. |
| 8,784,825 B2 | 7/2014 | Refaeli et al. |
| 8,828,723 B2 * | 9/2014 | Refaeli .................. C07K 14/82 435/372 |
| 8,986,702 B2 * | 3/2015 | Refaeli .................. A61K 39/00 424/185.1 |
| 9,150,831 B2 | 10/2015 | Cambier et al. |
| 9,365,825 B2 | 6/2016 | Turner et al. |
| 9,775,897 B2 * | 10/2017 | Refaeli .................. C07K 14/82 |
| 9,789,135 B2 | 10/2017 | Turner et al. |
| 10,442,853 B2 * | 10/2019 | Refaeli .................. A61K 39/00 |
| 2001/0049393 A1 | 12/2001 | Coller et al. |
| 2002/0076787 A1 | 6/2002 | Baetge et al. |
| 2002/0098166 A1 | 7/2002 | Havemann et al. |
| 2002/0155502 A1 | 10/2002 | Balint et al. |
| 2003/0072794 A1 | 4/2003 | Boulikas |
| 2003/0138859 A1 | 7/2003 | Barbera-Guillem et al. |
| 2003/0220286 A1 | 11/2003 | Abruzzese et al. |
| 2004/0224402 A1 | 11/2004 | Bonyhadi et al. |

(Continued)

FOREIGN PATENT DOCUMENTS

| | | |
|---|---|---|
| AU | 2762802 A1 | 5/2002 |
| AU | 2006304392 A1 | 4/2007 |

(Continued)

OTHER PUBLICATIONS

Altman, et al.,"Phenotypic Analysis of Antigen-Specific T Lymphocytes", Science 274: 94-96 (1996).
Andersen, et al.,"Parallel detection of antigen-specific T cell responses by combinatiorial encoding of MHC multimers", Nature Protocols 7(5): 891-902 (2012).
Chang, et al.,"Phenotypic expression in *E. coli* of a DNA sequence coding for mouse dihydrofolate reductase", Nature 275: 617-624 (1978).
DeBoer, et al., "The tac promoter: A functional hybrid derived from the trp and lac promoters", Proc. Natl. Acad. Sci. USA 80: 21-25 (1983).

(Continued)

*Primary Examiner* — Yan Xiao
(74) *Attorney, Agent, or Firm* — Foley & Lardner LLP

(57) ABSTRACT

Provided herein are methods and compositions for the treatment of melanoma using anti-tumor immune cells treated with a PTD-MYC fusion protein (e.g., an HIV TAT-MYC fusion protein).

5 Claims, 4 Drawing Sheets

Specification includes a Sequence Listing.

(56) References Cited

U.S. PATENT DOCUMENTS

| | | |
|---|---|---|
| 2005/0220705 A1 | 10/2005 | Brooks et al. |
| 2005/0281816 A1 | 12/2005 | Lamping et al. |
| 2006/0068369 A1 | 3/2006 | Coelho et al. |
| 2006/0068469 A1 | 3/2006 | Payne et al. |
| 2006/0115898 A1 | 6/2006 | Zhang et al. |
| 2006/0154331 A1 | 7/2006 | Avidan et al. |
| 2006/0156422 A1 | 7/2006 | Dalrymple et al. |
| 2006/0222657 A1 | 10/2006 | Dowdy et al. |
| 2007/0011753 A1 | 1/2007 | Ito et al. |
| 2007/0047583 A1 | 3/2007 | Assa et al. |
| 2007/0067854 A1 | 3/2007 | Habu et al. |
| 2007/0082397 A1 | 4/2007 | Hasson et al. |
| 2007/0093420 A1 | 4/2007 | Yeomans et al. |
| 2007/0098715 A1 | 5/2007 | Ettenberg et al. |
| 2007/0116691 A1 | 5/2007 | Cambier et al. |
| 2007/0130628 A1 | 6/2007 | Brown |
| 2007/0248618 A1 | 10/2007 | Cohen |
| 2009/0291094 A1 | 11/2009 | Refaeli et al. |
| 2010/0047217 A1 | 2/2010 | Refaeli et al. |
| 2010/0055129 A1 | 3/2010 | Refaeli et al. |
| 2010/0233804 A1 | 9/2010 | Zhou et al. |
| 2010/0279351 A1 | 11/2010 | Refaeli |
| 2010/0297763 A1 | 11/2010 | Cambier et al. |
| 2011/0218210 A1 | 9/2011 | Refaeli et al. |
| 2012/0003189 A1 | 1/2012 | Pelus et al. |
| 2012/0027792 A1 | 2/2012 | Pavlakis et al. |
| 2012/0244133 A1 | 9/2012 | Rosenberg et al. |
| 2012/0251563 A1 | 10/2012 | Nicchitta et al. |
| 2013/0177586 A1* | 7/2013 | Refaeli .............. C07K 14/82 424/192.1 |
| 2014/0109246 A1 | 4/2014 | Jimeno et al. |
| 2014/0255369 A1 | 9/2014 | Turner et al. |
| 2014/0356392 A1 | 12/2014 | Refaeli et al. |
| 2015/0164950 A1 | 6/2015 | Turner et al. |
| 2015/0218515 A1 | 8/2015 | Altrichter et al. |
| 2017/0044500 A1 | 2/2017 | Cooper et al. |
| 2018/0036396 A1 | 2/2018 | Refaeli et al. |

FOREIGN PATENT DOCUMENTS

| | | |
|---|---|---|
| CN | 1357620 A | 7/2002 |
| CN | 101330830 A | 12/2008 |
| EP | 0 367 76 A2 | 9/1981 |
| EP | 0 213 469 A2 | 3/1987 |
| EP | 1 103 615 A1 | 5/2001 |
| EP | 1 357 184 | 10/2003 |
| EP | 1 792 627 | 6/2007 |
| GB | 2 387 599 | 10/2003 |
| JP | 2000-189157 | 7/2000 |
| JP | 2001-518300 | 10/2001 |
| JP | 2002-541786 A | 12/2002 |
| JP | 2003-513672 A | 4/2003 |
| JP | 2003-514565 | 4/2003 |
| JP | 2004-519245 A | 7/2004 |
| JP | 2005-523012 | 8/2005 |
| JP | 2005-525085 | 8/2005 |
| JP | 2005-527211 | 9/2005 |
| JP | 2009-511081 A | 3/2009 |
| JP | 2011-528567 A | 11/2011 |
| JP | 2012-501347 A | 1/2012 |
| JP | 2014-527980 A | 10/2014 |
| JP | 6167130 B2 | 8/2015 |
| JP | 2015-525209 A | 9/2015 |
| JP | 2016-510996 A | 4/2016 |
| JP | 6484293 B2 | 3/2019 |
| WO | WO-86/03780 A1 | 7/1986 |
| WO | WO-92/15322 | 9/1992 |
| WO | WO-94/04686 | 3/1994 |
| WO | WO-94/19465 | 9/1994 |
| WO | WO-95/14078 | 5/1995 |
| WO | WO-98/10058 | 3/1998 |
| WO | WO-98/52614 | 11/1998 |
| WO | WO-99/16884 | 4/1999 |
| WO | WO-99/45962 | 9/1999 |
| WO | WO-99/53023 | 10/1999 |
| WO | WO-99/53028 | 10/1999 |
| WO | WO-00/09669 | 2/2000 |
| WO | WO-00/61617 A2 | 10/2000 |
| WO | WO-00/62067 | 10/2000 |
| WO | WO-01/34824 A2 | 5/2001 |
| WO | WO-01/38548 | 5/2001 |
| WO | WO-02/057436 | 7/2002 |
| WO | WO-02/074968 A1 | 9/2002 |
| WO | WO-03/020763 | 3/2003 |
| WO | WO-03/033701 | 4/2003 |
| WO | WO-03/038057 | 5/2003 |
| WO | WO-03/039462 | 5/2003 |
| WO | WO-03/057171 | 7/2003 |
| WO | WO-03/089580 | 10/2003 |
| WO | WO-03/089630 | 10/2003 |
| WO | WO-03/094849 | 11/2003 |
| WO | WO-03/097675 | 11/2003 |
| WO | WO-2004/033685 | 4/2004 |
| WO | WO-2004/035535 | 4/2004 |
| WO | WO-2004/044004 | 5/2004 |
| WO | WO-2004/050885 | 6/2004 |
| WO | WO-2004/074322 | 9/2004 |
| WO | WO-2004/084805 | 10/2004 |
| WO | WO-2005/014785 | 2/2005 |
| WO | WO-2005/084158 | 9/2005 |
| WO | WO-2005/113595 | 12/2005 |
| WO | WO-2005/114215 | 12/2005 |
| WO | WO-2006/000830 | 1/2006 |
| WO | WO-2006/032876 | 3/2006 |
| WO | WO-2006/116512 | 11/2006 |
| WO | WO-2006/125962 | 11/2006 |
| WO | WO-2007/047583 A2 | 4/2007 |
| WO | WO-2007/067183 | 6/2007 |
| WO | WO-2008/038002 | 4/2008 |
| WO | WO-2008/039818 | 4/2008 |
| WO | WO-2008/112922 | 9/2008 |
| WO | WO-2009/059304 | 5/2009 |
| WO | WO-2009/139930 A2 | 11/2009 |
| WO | WO-2010/011644 | 1/2010 |
| WO | WO-2010/025421 | 3/2010 |
| WO | WO-2011/100477 A2 | 8/2011 |
| WO | WO-2012/055170 | 5/2012 |
| WO | WO-2013/039889 | 3/2013 |
| WO | WO-2013/166321 | 11/2013 |
| WO | WO-2014/018863 | 1/2014 |
| WO | WO-2014/083173 | 6/2014 |
| WO | WO-2014/133567 | 9/2014 |
| WO | WO-2014/133568 | 9/2014 |
| WO | WO-2014/164606 A1 | 10/2014 |
| WO | WO-2016/105542 | 6/2016 |
| WO | WO-2017/123978 A1 | 7/2017 |

OTHER PUBLICATIONS

Derossi, et al., "Trojan peptides: the penetratin system for intracellular delivery", Trends Cell Biol. 8: 84-87 (1998).

Elliot, et al.,"Intercellular Trafficking and Protein Delivery by a Herpesvirus Structural Protein", Cell 88: 223-233 (1997).

Goeddel, et al. "Synthesis of human fibroblast interferon by *E. coli*", Nucleic Acids Res. 8: 4057-4074 (1980).

Goeddel, et al.,"Direct expression in *Escherichia coli* of a DNA sequence coding for human growth hormone", Nature 281: 544-548 (1979).

Henikoff. et al.,"Amino acid substitution matrices from protein blocks", Proc. Natl Acad. Sci. USA, 89: 10915-10919 (1992).

Schwarze, et al.,"In vivo protein transduction: intracellular delivery of biologically active proteins, compounds and DNA", Trends Pharmacol. Sci., 21: 45-48 (2000).

Siebenlist, et al.,"*E. coli* RNA Polymerase Interacts Homologously with Two Different Promoters", Cell 20: 269-281 (1980).

A. Strasser, et al., "Novel primitive lymphoid tumours induced in transgenic mice by cooperation between myc and bcl-2", Letters to Nature 348: 331-333 (1990).

Chinese Office Action, issued in Chinese Pat. App. No. 201510760532. X, 14 pages (dated Jan. 10, 2020).

Notice of Allowance on U.S. Appl. No. 16/042,904 dated Jan. 29, 2020.

(56) References Cited

OTHER PUBLICATIONS

Aubry et al., "N-Myc Shares Cellular Functions with c-Myc", DNA and Cell Biology, vol. 19, No. 6, Jun. 2000, pp. 353-364.
Australian Examination Report, issued in Australian Pat. App. No. 2018247295, 2 pages (dated Dec. 6, 2019).
Australian Examination Report, issued in Australian Patent Application No. 2014249200, 4 pages (dated Mar. 15, 2019).
Austrian Search Report and Written Opinion received for Singapore Patent Application No. 201101367-9, dated Mar. 23, 2012, 17 pages.
Baum, Christopher, "Insertional Mutagenesis in Gene Therapy and Stem Cell Biology", Current Opinion in Hematology, vol. 14, Jul. 2007, pp. 337-342.
Beerens et al., "Protein Transduction Domains and their Utility in Gene Therapy", Current Gene Therapy, vol. 3, No. 5, 2003, pp. 486-494.
Benassayag et al., "Human c-Myc Isoforms Differentially Regulate Cell Growth and Apoptosis in *Drosophila melanogaster*," Molecular and Cellular Biology 25(22): 9897-9909 (2005).
Berkson et al., "Pilot Screening Programme for Small Molecule Activators of p53", International Journal of Cancer, vol. 115, 2005, pp. 701-710.
Bissonnette et al., "Apoptotic cell death induced by c-myc is inhibited by bcl-2," Nature, vol. 359, Oct. 8, 1992, pp. 552-554.
Bouchard et al., "Control of cell proliferation by Myc", Trends in Cell Biology, vol. 8, pp. 202-206, (1998).
Bunting et al., "Restoration of lymphocyte function in Janus kinase 3-deficient mice by retro-viral-mediated gene transfer," Nature Medicine 4:58-64 (1998).
Buske et al., "Deregulated Expression of HOXB4 Enhances the Primitive Growth Activity of Human Hematopoietic Cells", Blood, vol. 100, No. 3, Aug. 1, 2002, pp. 862-868.
Canadian Office Action on CA 2905285 dated Jan. 30, 2020.
Canadian Office Action on CA 2905296 dated Jan. 31, 2020.
Canadian Office Action, dated Jul. 4, 2018, issued in corresponding Canadian Patent Application No. 2,626,525.
Canadian Office Action, issued in Canadian Pat. App. No. 2905285, 5 pages (dated Jan. 30, 2020).
Canadian Office Action, issued in Canadian Pat. App. No. 2905296, 4 pages (dated Jan. 31, 2020).
Canadian Office Action, issued in Canadian Pat. App. No. 3035209, 4 pages (dated Feb. 3, 2020).
Canadian Office Action, issued in corresponding CA Pat. App. No. 2879667, 4 pages (dated Jun. 18, 2019).
Capecchi, Mario R., "Altering the Genome by Homologous Recombination", Science, vol. 244, No. 4910, Jun. 16, 1989, pp. 1288-1292.
Caron, et al., "Endosome disruption enhances the functional nuclear delivery of Tat-fusion proteins", Biochem Biophys Res Commun, (2004), vol. 319, pp. 12-20.
Carotta et al., "Directed Differentiation and Mass Cultivation of Pure Erythorid Progenitors from Mouse Embryonic Stem Cells", Blood, vol. 104, No. 6, Sep. 15, 2004, pp. 1873-1880.
Chadwick, et al., "Notch Signaling Induces Apoptosis in Primary Human CD34 Hematopoietic Progenitor Cells", Stem Cells, (2007), vol. 24, pp. 203-210.
Chang, et al., "Phenotypic expression in *E. coli* of a DNA sequence coding for mouse dihydrofolate reductase," Nature, vol. 275, Oct. 19, 1978, pp. 617-624.
Chen et al., "Small-Molecule Anthracene-Induced Cytotoxicity and Induction of Apoptosis through Generation of Reactive Oxygen Species", Biological & Pharmaceutical Bulletin, vol. 27, No. 6, Jun. 2004, pp. 838-845.
Cheng et al., "BCL-2, BCL-XL, Sequester BH3 Domain-Only Molecules Preventing BAX- and BAK-Mediated Mitochondrial Apoptosis", Molecular Cell (2001) vol. 8, pp. 705-711.
Chi, et al., "Physical Stability of Proteins in Aqueous Solution: Mechanism and Driving Forces in Nonnative Protein Aggregation," Pharm. Res., vol. 20, No. 9, Sep. 2003, pp. 1325-1336.

Chin et al., "Essential Role for Oncogenic Ras in Tumour Maintenance", Nature, vol. 400, 1999, pp. 468-472.
Chinese 3rd Office Action dated Nov. 28, 2016 in Chinese Patent Application No. 201410168106.2.
Chinese Office Action, dated May 24, 2018, issued in corresponding Chinese Patent Application No. 201380048261.4.
Choi et al., "Myc Protein is Stabilized by Suppression of a Novel E3 Ligase Complex in Cancer Cells", Genes & Development, vol. 24, 2010, pp. 1236-1241.
Choi, et al., "Status Epilepticus-Induced Somatostatinergic Hilar Interneuron Degeneration Is Regulated by Striatal Enriched Protein Tyrosine Phosphatase", Journal of Neuroscience, (2007), vol. 27, No. 11, pp. 2999-3009.
Cleland, et al., "The development of stable protein formulations: a close look at protein aggregation, deamidation, and oxidation," Crit. Rev. Ther. Drug Carrier Syst., vol. 70, No. 4, Jan. 1, 1993, pp. 307-377.
Coeytaux et al., "The Cationic Amphipathic alpha-Helix of HIV-1 Viral Protein R (Vpr) Binds to Nucleic Acids, Permeabilizes Membranes, and Efficiently Transfects Cells," The Journal of Biological Chemistry, vol. 278, No. 20, May 16, 2003, pp. 18110-18116.
Coller, et al., "Expression Analysis with Oligonucleotide Microarrays Reveals that MYC Regulates Genes Involved in Growth, Cell Cycle, Signaling, and Adhesion", PNAS, (2000), 97(7):3260-3265.
Conti, et al., "Gene therapy using neural stem cells," Methods Mol. Biol. 198:233-244 (2002).
Coppola et al., "Constitutive c-myc oncogene expression blocks mouse erythroleukaemia cell differentiation but not commitment," Nature, vol. 320, Apr. 24, 1986, pp. 760-763.
Corrected Notice of Allowability on U.S. Appl. No. 15/179,735 dated Jun. 8, 2018.
Corrected Notice of Allowability on U.S. Appl. No. 15/179,735 dated Jun. 15, 2018.
Corrected Notice of Allowability on U.S. Appl. No. 16/042,904 dated Mar. 6, 2020.
Corrected Notice of Allowance on U.S. Appl. No. 15/717,675 dated Jan. 10, 2020.
D'Alessandro, et al., "Red blood cell storage: the story so far", Blood Transfus 8: 82-88 (2010).
Dang et al., "Identification of the Human c-myc Protein Nuclear Translocation Signal", Molecular and Cellular Biology, vol. 8, No. 10, Oct. 1988, pp. 4048-4054.
Dang et al., "Nuclear and Nucleolar Targeting Sequences of c-erb-A, c-myb, N-myc, p53, HSP70 and HIV tat Proteins". Journal of Biological Chemistry, vol. 264, No. 30, pp. 18019-18023 (1989).
Dang, Chi V., "c-Myc Target Genes Involved in Cell Growth, Apoptosis, and Metabolism", Molecular and Cellular Biology, vol. 19, No. 1, Jan. 1999, pp. 1-11.
Daugas, et al., "Erythrocytes: Death of a mummy", Cell Death and Differentiation 8(12): 1131-1133 (2001).
De Korte, "New additive solutions for red cells", ISBT Science Series 11: 165-170 (2016).
Deboer, et al., "The tac promoter: A functional hybrid derived from the trp and lac promoters," Proc. Natl. Acad. Sci. vol. 80, Jan. 1983, pp. 21-25.
Decision of Rejection issued on Japanese application 2014-108137, dated Jun. 2, 2016, English translation only.
Decision of Rejection, issued in Chinese Patent Application No. 201380048261.4, 6 pages (dated Apr. 16, 2019).
Delgado et al., "Myc Roles in Hematopoiesis and Leukemia," Genes and Cancer, 2010, pp. 605-616.
Deocampo, et al., "Cooperation of BCL-2 and MYC in the Neoplastic Transformation of Normal Rat Lever Epithelial Cells is Related to the Down-Regulation of Gap Junction-Mediated Intercellular Communication", Carcinogenesis, vol. 21, No. 8, pp. 1501-1506,(2000).
Derossi, et al., "Trojan peptides: the penetratin system for intracellular delivery," Cell Biology, vol. 8, Feb. 1998, pp. 84-87.
Dmitrovsky et al., "A Transfected c-myc Oncogene Inhibits Mouse Erytholeukemic Differentiation," Current Topics in Microbiology and Immunology, vol. 132, 1986, 4 pages.

(56) References Cited

OTHER PUBLICATIONS

Domashenko et al., "TAT-mediated transduction of NF-Ya peptide induces the ex vivo proliferation and egraftment potential of human hematopoietic progenitor cells," Blood, Oct. 14, 2010, vol. 116, No. 15, pp. 2676-2683.
Dvorak et al., "Cytochemical Localization of Peroxidase Activity in the Developing Erythrocyte," Am. J. Pathol. 1972, 67(2), pp. 303-326.
Eilers, et al., "Chimeras of MYC Oncoprotein and Steroid Receptors Cause Hormone-Dependent Transformation of Cells," Nature 340(6228):66-68 (1989).
Eischen, et al., "Apoptosis Triggered by Myc-Induced Suppression of Bcl-XL or Bcl-2 Is Bypassed during Lymphomagenesis", Molecular Cell Biology, 2001, 21: 5063-5070.
Elliot, et al., "Intercellular Trafficking and Protein Delivery by a Herpesvirus Structural Protein," Cell, vol. 88, Jan. 24, 1997, pp. 223-233.
English Translation of Decision of Rejection on Japanese Application No. 2011-520133, dated Nov. 26, 2014, 6 pages.
English Translation of Decision of Rejection on Japanese Application No. 2011-525258, dated Dec. 3, 2014, 11 pages.
English Translation of Fourth Office Action received for Chinese Patent Application No. 200880015602.7 dated Nov. 11, 2013, 6 pages.
English Translation of Notification of Reasons of Refusal for Japanese Patent Application No. 2012-221023 dated Jun. 24, 2014, 2 pages.
English Translation of Office Action on Chinese Appln. No. 200980127166.7 dated Apr. 11, 2014, 3 pages.
English Translation of Office Action on Israeli Application No. 208810 dated Jan. 13, 2015, 3 pages.
English Translation of Office Action on Israeli Application No. 232432 dated Mar. 8, 2015, 3 pages.
English Translation of Office Action on Israeli Patent Application No. 200919 dated May 19, 2014, 3 pages.
English Translation of Office Action on Japanese Patent Application. No. 2012-221023 dated Apr. 22, 2014, 3 pages.
English Translation of Office Action on Korean Patent Application No. 10-2013-7020078 dated Sep. 17, 2014, 5 pages.
English Translation of Office Action received for Chinese Patent Application No. 200980126312.4 dated Jan. 22, 2014, 3 pages.
English Translation of Office Action received for Eurasian Patent Application No. 201001762/28, posted Oct. 16, 2013, 1 page.
English translation of Office Action received for Israeli Patent Application No. 190946, dated Apr. 22, 2013, 1 page.
English Translation of Office Action received for Israeli Patent Application No. 209968 dated Jan. 2, 2014, 2 pages.
English translation of Office Action received for Japanese Application No. 2008-536713 dated Aug. 5, 2013, 2 pages.
English Translation of Office Action received for Japanese Patent Application No. 2011-525258 dated Feb. 17, 2014, 4 pages.
English Translation of Office Action received for Korean Patent Application No. 10-2008-7011791 dated Jan. 15, 2014, 3 pages.
English Translation of Office Action received for Korean Patent Application No. 10-2013-7028338, dated Jan. 15, 2014, 3 pages.
English Translation of Second Office Action received for Chinese Patent Application No. 200980127166.7, dated Jun. 10, 2013, 1 page.
English Translation of the Third Office Action on Chinese Patent Application No. 200680045545.8 dated Feb. 15, 2015, 4 pages.
English Translation of Third Office Action on Japanese Patent Application No. 2009-553785 dated Apr. 22, 2014, 3 pages.
EPO Communication under Rule 161 and 162, issued in EP Pat. App. No. 17876016.1, 3 pages (dated Jul. 9, 2019).
Esdar, C., et al., "Differentiation-associated apoptosis of neural stem cells is effected by Bcl-2 overexpression: impact on cell lineage determination," Eur. J. Cell Biol.,(2001), vol. 80, No. 8, pp. 539-553.
European Extended Search Report, issued in EP Pat. App. No. 17920607.3, 7 pages (dated Dec. 11, 2019).
European Extended Search Report, issued in European Patent Appln. No. 19157513.3, 13 pages (dated Apr. 1, 2019).
European Office Action, dated Jun. 29, 2018, issued in corresponding European Patent Appln. No. 14779483.8.
European Office Action, dated May 15, 2018, issued in corresponding European Patent Application No. 09747016.5.
European Office Action, issued in corresponding EP Pat. App. No. 14779483.8, 4 pages (dated Jun. 28, 2019).
European Office Action, issued in EP Pat. App. No. 13820331.0, 3 pages (dated Jul. 29, 2019).
European Office Action, issued in EP Pat. App. No. 14779483.8, 4 pages (dated Jan. 14, 2019).
European Office Action, issued in European Pat. App. No. 18154875.1, 4 pages (dated Sep. 6, 2019).
Examination Report for Indian Patent Application No. 3332/DELNP/2008 dated Aug. 23, 2013, 6 pages.
Examination Report issued on Australian Application 2013292330, dated Sep. 6, 2017.
Examination Report issued on Australian Application 2015205879, dated Mar. 15, 2016.
Examination Report issued on Australian Application 2016203892, dated Apr. 12, 2017.
Examination Report issued on EP Application 09747016.5, dated Jul. 26, 2016.
Examination Report issued on EP Application 13820331.0, dated Apr. 24, 2018.
Examination Report issued on EP Application 14778538.0, dated Apr. 16, 2018.
Examination Report issued on European Application 14779483.8, dated Oct. 16, 2017.
Examination Report issued on Indian Application 2048/DELNP/2011, dated Sep. 15, 2016.
Examination Report issued on Indian Application 634/DELNP/2011, dated Jun. 8, 2017.
Examination Report issued on Indian Application 9033/DELNP/2010, dated May 19, 2017.
Examination Report on Australian application 2009274172, dated Jul. 24, 2014, 3 pages.
Examination Report on Australian Patent Application No. 2012216462 dated Mar. 6, 2014, 3 pages.
Examination Report on Canadian Application 2,731,767, dated Sep. 5, 2014, 2 pages.
Examination Report on Canadian Application No. 2,735,522 dated Oct. 2, 2014, 2 pages.
Examination Report on European Application No. 09747016.5 dated Mar. 19, 2015, 5 pages.
Examiner's Report on Canadian Application No. 2680613 dated Nov. 28, 2014, 4 pages.
Examiner's Report on Canadian Application No. 2723114 dated Apr. 21, 2015, 4 pages.
Examiner's Report on European Application No. 12187097.6 dated Jan. 22, 2015, 6 pages.
Extended European Search Report and Search Opinion received for Patent Application No. 12187097.6, dated Mar. 27, 2013, 8 pages.
Extended European Search Report for EP Patent Application No. 13188850.0, dated May 27, 2014, 8 pages.
Extended European Search Report received for European Patent Application No. 09810692.5, dated Jul. 11, 2011, 5 pages.
Extended European Search Report received for European Patent Application No. 09747016.5, dated May 30, 2012, 8 pages.
Extended European Search Report received for European Patent Application No. 09800871. 7, dated Jun. 24, 2011, 5 pages.
Extended European Search Report received for European Patent Application No. 12187077.8, dated Mar. 25, 2013, 7 pages.
Extended Search Report issued on EP Application 13820331.0, dated Oct. 10, 2016.
Extended Search Report issued on European Application 14778538.0, dated Sep. 29, 2016.
Extended Search Report issued on European Application 14779483.8, dated Dec. 23, 2016.
Extended Search Report issued on European Patent Application 15175802.6, dated Dec. 14, 2015.

(56) References Cited

OTHER PUBLICATIONS

Fanidi et al., "Cooperative interaction between c-myc and bcl-2 proto-oncogenes," Nature, vol. 359, Oct. 8, 1992, pp. 554-556.
Felsher, et al., "Reversible Tumorigenesis by MYC in Hematopoietic Lineages", (1999), Molecular Cell, 4: 199-207.
Final Office Action on U.S. Appl. No. 12/467,957, dated Sep. 17, 2014, 9 pages.
Final Office Action on U.S. Appl. No. 12/506,894 dated Oct. 9, 2014, 15 pages.
Final Office Action on U.S. Appl. No. 13/797,648 dated Feb. 8, 2017.
Final Office Action on U.S. Appl. No. 14/461,105 dated Sep. 15, 2016.
Final Office Action on U.S. Appl. No. 14/509,870 dated Feb. 3, 2017.
Final Office Action on U.S. Appl. No. 14/873,296, dated Jan. 24, 2018.
Final Office Action on U.S. Appl. No. 15/244,138 dated Jun. 4, 2018.
Final Office Action on U.S. Appl. No. 12/701,383 dated Nov. 13, 2014, 18 pages.
Final Office Action on U.S. Appl. No. 13/795,659 dated Jul. 11, 2014, 16 pages.
Final Office Action on U.S. Appl. No. 13/795,659 dated Mar. 26, 2015, 18 pages.
Final Office Action on U.S. Appl. No. 13/797,648 dated Apr. 1, 2015, 12 pages.
Final Office Action on U.S. Appl. No. 15/244,138 dated Mar. 14, 2019.
Final Office Action on U.S. Appl. No. 15/668,451 dated May 24, 2018.
Final Office Action on U.S. Appl. No. 15/717,675 dated Jun. 27, 2019.
Final Office Action on U.S. Appl. No. 16/042,904 dated Nov. 1, 2019.
Final Office Action on U.S. Appl. No. 11/583,970 dated Apr. 9, 2014, 20 pages.
Final Office Action received for Korean Patent Application No. 10-2009-7021320, dated May 29, 2013, 6 pages (3 pages of English Translation and 3 pages of Office Action).
Final Office Action received for U.S. Appl. No. 11/583,970, dated Nov. 17, 2011, 15 pages.
Final Office Action received for U.S. Appl. No. 12/701,383 , dated Nov. 16, 2011, 13 pages.
Final Office Action received for U.S. Appl. No. 11/583,970, dated Nov. 26, 2008, 13 pages.
Final Office Action received for U.S. Appl. No. 12/048,148, dated Feb. 15, 2013, 17 pages.
Final Office Action received for U.S. Appl. No. 12/467,957 dated Feb. 28, 2011, 8 pages.
Final Office Action received for U.S. Appl. No. 12/550,166, dated May 11, 2012, 12 pages.
Final Office Action received on U.S. Appl. No. 11/583,970, dated Nov. 4, 2009, 10 pages.
First Examination Report on Australian Application No. 2014202016 dated May 12, 2015, 3 pages.
First Examination Report, issued in Indian Patent Application No. 6624/DELNP/2014, 4 pages (dated Sep. 27, 2018).
First Office Action issued on Chinese Application 201410479685.2, dated Nov. 17, 2015.
First Office Action, issued in JP Pat. App. No. 2019-512193, 8 pages (dated Sep. 30, 2019).
Futaki,Chemistry and Biology (Kagaku to Seibutsu), vol. 43, No. 10, Oct. 1, 2005, p. 649-653 (English translation not available).
Gandarillas et al., "C-Myc promotes differentiation of human epidermal stem cells," Genes & Develoopment, vol. 11, 1997, pp. 2869-2882.
Gauss et al., "DEAE-Dextran Enhances Electroportation of Mammalian Cells", Nucleic Acids Research, vol. 20, No. 4, pp. 6739-6740 (1992).
Goeddel, et al., "Direct expression in *Escherichia coli* of a DNA sequence coding for human growth hormone," Nature, vol. 281, Oct. 18, 1979, p. 544.
Goeddel, et al., "Synthesis of human fibroblast interferon by *E. coli*," Nucleic Acids Research, vol. 8, Aug. 12, 1980, p. 4057.
Grumont et al., "The Mitogen-Induced Increase in T Cell Size Involves PKC and NFAT Activation of Rel/NF-kB-Dependent c-myc Expression," Immunity, 2004, vol. 21, p. 19-30.
Guzman et al., "Preferential induction of apoptosis for primary human leukemic stem cells," PNAS 99(25):16220-16225 (2002).
Habib et al., "Myc Stimulates B Lymphocyte Differentiation and Amplifies Calcium Signaling", J.Cell Biol., vol. 179, No. 4, 2007, pp. 717-731.
Hann et al., "Proteins Encoded by the Human C-Myc Oncogene: Differential Expression in Neoplastic Cells", Mol. Cell. Biol., vol. 4, No. 11, Nov. 1984, pp. 2486-2497.
Heinkoff, et al., "Amino acid substitution matrices from protein blocks," Proc. Natl Acad. Sci. USA, vol. 89, Nov. 1992, pp. 10915-10919.
Hiramatsu, et al., "Complete reconstitution of human lymphocytes from cord blood CD34 cells using the NOD/SCID/? c null mice model", Blood 102(3): 873-880 (2003).
Hirose, et al., "Immortalization of Erythroblasts by c-MYC and BCL-XL Enables Large-Scale Erythrocyte Production from Human Pluripotent Stem Cells", Stell Cell Reports I: 499-508 (2013).
Ho, et al., "Synthetic Protein Transduction Domains: Enhanced Transduction Potential in Vitro and in Vivo", Cancer Research, (2001), vol. 61, pp. 474-477.
Hoffman, "Progress in the develoment of systems for in vitro expansion of human hematopoietic stem cells," Curr. Op. Hematology 6(3): 14 pages (1999).
Horton, S.J. et al., "Continuous MLL-ENL expression is necessary to establish a "Hox Code" and maintain immortalization of hematopoietic progenitor cells," Cancer Res. 65(20):9245-9252 (2005).
Hoshimaru, M. et al., "Differentiation of the immortalized adult neuronal progenitor cell line HC2S2 into neurons by regulatable suppression of the V-MYC oncogene," Proceedings of the National Acadamy of Sciences of USA 93(4):1518-1523 (1996).
Howard, M.J. et al., "Transplantation of apoptosis-resistant embryonic stem cells into the injured rat spinal cord," Somatosensory & Motor Research 22(1-2):37-44 (2005).
Huang et al., "Dynamic Regulation of C-Myc Proto-Oncogene Expression during Lymphocyte Development Revealed by a GFP-c-Myc Knock-In Mouse", Eur. J. Immunol., vol. 38, No. 2, 2008, pp. 342-349.
Huang, et al., "Negative Control of the Myc Protein by the Stress-Responsive Kinase Pak2," Molecular and Cellular Biology, vol. 24, No. 4, Feb. 2001, pp. 1582-1594.
Huettner et al., "Reversibility of Acute B-Cell Leukaemia Induced by BCR-ABL 1," Nature Genetics, vol. 24, 2000, pp. 57-60.
Indian First Examination Report, issued in Indian Pat. App. No. 9205/DELNP/2015, 8 pages (dated Nov. 28, 2019).
Indian First Examination Report, issued in Indian Pat. App. No. 9206/DELNP/2015, 6 pages (dated Dec. 26, 2019).
International Preliminary Report and Written Opinion for International Application No. PCT/US2014/022971, dated Sep. 24, 2015.
International Preliminary Report on Patentability for International Application No. PCT/US2013/051384, dated Jan. 29, 2015, 12 pages.
International Preliminary Report on Patentability issued on PCT/US2014/022977, dated Sep. 15, 2015.
International Preliminary Report on Patentability on PCT/US2017/045336 dated Feb. 13, 2020.
International Preliminary Report on Patentability received for PCT Patent Application No. PCT/US2006/040379, dated Apr. 23, 2008, 5 pages.
International Preliminary Report on Patentability received for PCT Patent Application No. PCT/US2008/056896, dated Sep. 15, 2009, 4 pages.
International Preliminary Report on Patentability received for PCT Patent Application No. PCT/US2008/082263, dated May 4, 2010, 6 pages.

(56) References Cited

OTHER PUBLICATIONS

International Preliminary Report on Patentability Received for PCT Patent Application No. PCT/US2009/003105, dated Nov. 17, 2010, 6 pages.
International Preliminary Report on Patentability received for PCT Patent Application No. PCT/US2009/051242, dated Jan. 25, 2011, 6 pages.
International Preliminary Report on Patentability received for PCT Patent Application No. PCT/US2009/055443, dated Mar. 1, 2011, 6 pages.
International Preliminary Report on Patentability, issued in Int'l. App. No. PCT/US2017/064206, 13 pages (dated Jun. 13, 2019).
International Preliminary Report on Patentability, issued in Int'l. App. No. PCT/US2018/044740, 9 pages (dated Feb. 13, 2020).
International Search Report and Written Opinion for International (PCT) Patent Application No. PCT/US06/040379, dated Sep. 24, 2007, 6 pages.
International Search Report and Written Opinion for International Application No. PCT/US2013/051384, dated Nov. 13, 2013, 15 pages.
International Search Report and Written Opinion for International Application No. PCT/US2014/022971 dated Aug. 13, 2014, 12 pages.
International Search Report and Written Opinion for PCT/US2017/064206, dated Mar. 19, 2018.
International Search Report and Written Opinion from PCT/US06/40379 dated Sep. 24, 2007.
International Search Report and Written Opinion on PCT/US2014/022977, dated Aug. 28, 2014, 13 pages.
International Search Report and Written Opinion received for PCT Patent Application No. PCT/US2008/056896 dated Aug. 14, 2008, 5 pages.
International Search Report and Written Opinion received for PCT Patent Application No. PCT/US2008/082263, dated Jun. 25, 2009, 8 pages.
International Search Report and Written Opinion received for PCT Patent Application No. PCT/US2009/003105, dated Jan. 15, 2010, 9 pages.
International Search Report and Written Opinion received for PCT Patent Application No. PCT/US2009/051242, dated Feb. 19, 2010, 9 pages.
International Search Report and Written Opinion received for PCT Patent Application No. PCT/US2009/055443, dated Jun. 30, 2010, 11 pages.
International Search Report and Written Opinion, dated Oct. 16, 2018, issued in International Application No. PCT/US2018/044740 (13 pages).
International Search Report and Written Opinion, issued in Int'l. App. No. PCT/US2019/062200, 13 pages (dated Jan. 16, 2020).
Invitation for European Application No. 09810692.5 dated Feb. 25, 2014, 3 pages.
Invitation issued on EP Application 15175802.6, dated Jan. 31, 2017.
Invitation to Pay Additional Fees and, Where Applicable, Protest Fee for PCT Application No. PCT/US2014/22971, dated May 27, 2014, 2 pages.
IPRP from PCT/US09/55443 dated Mar. 1, 2011.
Iritani et al., "Modulation of T-lymphocyte development, growth and cell size by the Myc antagonist and transcriptional repressor Mad 1", The EMBO Journal, vol. 21, No. 18, pp. 4820-4830, 2002.
Israeli Office Action, dated Jul. 29, 2018, issued in corresponding Israeli Patent Application No. 256512.
Israeli Office Action, dated Jul. 30, 2018, issued in Israeli Patent Application No. 241192.
Israeli Office Action, dated Jun. 27, 2018, issued in corresponding Israeli Patent Application No. 208810.
Jadlowsky, et al., "Dominant negative mutant Cyclin T1 proteins inhibit HIV transcription by specifically degrading Tat", Retrovirology, vol. 5, Article 63, 12 pages (2008).
Japanese Office Action on JP 2019-006759 dated Feb. 20, 2020.

Japanese Office Action, dated Jul. 18, 2018, issued in corresponding Japanese Patent Application No. 2017-123838.
Japanese Office Action, issued in Japanese Patent Application No. 2018-017287, 13 pages (dated Apr. 18, 2019).
Japanese Office Action, issued in Japanese Patent Application No. 2018-048138, 3 pages (dated Feb. 12, 2019).
Japanese Office Action, issued in Japanese Patent Appln. No. 2017-166334, 6 pages (dated Apr. 24, 2019).
Japanese Office Action, issued in Japanese Patent Appln. No. 2018-048138, 4 pages (dated Feb. 12, 2019).
Japanese Office Action, issued in JP Pat. App. No. 2018-153567, 8 pages (dated Jul. 25, 2019).
Jayapal et al., "Down-regulation of Myc is Essential for Terminal Erythroid Maturation" The Journal of Biological Chemistry, vol. 285, No. 51, pp. 40252-40265, Dec. 17, 2010.
Johnson, N.A. et al., "Lymphomas with concurrent BCL2 and MYC translocations: the critical factors associated with survival", Blood, 2009, vol. 114, No. 11, pp. 2273-2279.
Kaptein, et al., "Anti-IgM-mediated Regulation of c-myc and Its Possible Relationship to Apoptosis," JBC, vol. 271, No. 31, Aug. 2, 1996, pp. 18875-18884.
Karon, et al., "Temporal sequence of major biochemical events during Blood Bank storage of packed red blood cells", Blood Transfus 10: 453-461 (2012).
Kashio, et al., "A Protein Derived From the Fusion of TAT Peptide and FNK, a Bcl-xL Derivative, Prevents Cochlear Hair Cell Death From Aminoglycoside Ototoxicity In Vivo", Journal of Neuroscience Research, (2007), vol. 85, No. 7, pp. 1403-1412.
Kelso et al., "Survival of the Myeloid Progenitor Cell Line FDC-P1 is Prolonged by Interferon-y or Interleukin-4", Growth Factors, vol. 6, No. 3, 1992, pp. 233-242.
Kitada, et al., "Reversal of Chemoresistance of Lymphoma Cells by Antisense-Mediated Reduction of bcl-2 Gene Expression", Antisense Research and Development, (1994), vol. 4, pp. 71-79.
Korbling et al., "Allogenic Blood Stem Cell Transplantation: Peripheralization and Yield of Donor-Derived Primitive Hematopoietic Progenitor Cells (CD34+Thy-Idim) and Lymphoid Subsets, and Possible Predictors of Engraftment and Graft-Versus-Host Disease," Blood 86:2842-2848 (1995).
Krosl et al., "In vitro expansion of hematopoietic stem cells by recombinant TAT-HOXB4 protein," Nature Mediciine 9(11):1428-1432 (2003).
Laurentl, et al., "Hematopoietic Stem Cell Function and Survival Depend on c-Myc and N-Myc Activity", Cell Stem Cell 3: 611-624 (2008).
Levesque, J-P et al., "The endosteal 'osteoblastic' niche and its role in hematopoietic stem cell homing and mobilization", Leukemia, 2010, vol. 24, pp. 1979-1992.
Li et al., "Reconstitution of Functional Human B Lymphocytes in NOD/SCID Mice Engrafted with ex vivo Expanded CD34 Cord Blood Cells", Experimental Hematology, vol. 30, 2002, pp. 1036-1043.
Macpherson, P. et al., "Activity-dependent gene regulation in conditionally-immortalized muscle precursor cell lines," J. Cell. Biol. 91(4):821-839 (2004).
Matte, et al., "Erythropoietin Can Promote Erythroid Progenitor Survival by Repressing Apoptosis Through Bcl-XL, and Bcl-2", Blood Journal 88(5): 1576-1582 (1996).
McCarthy, "Underground movement", Nature Reviews Cancer, (2007), vol. 7, 1 page, published online Oct. 11, 2007.
Melkonyan et al., "Electroporation efficiency in mammalian cells is increased by dimethyl sulfoxide (DMSO)," Nucleic Acids Research 24:4356-4357 (1996).
Merino et al., "Developmental Regulation of the Bcl-2 Protein and Susceptibility to Cell Death in B Lymphocytes", The EMBO Journal, vol. 13, No. 3, 1994, pp. 683-691.
Miharada et al., "Efficient enucleation of erythroblasts differentiated in vitro from hematopoietic stem and progenitor cells", Nature Biotechnology, 24(10): 1255-1256, 2006.
Miller et al., "Expansion in vitro of adult murine hematopoietic stem cells with transplantable lympho-myeloid reconstituting ability," PNAS USA 94: 13648-13653 (1997).

(56) References Cited

OTHER PUBLICATIONS

Momir, et al., "Is erythropoietin a survival factor for red blood cells", Journal of the American Society of Nephrology, 7(8): 1178-1182 (1996).
Moore et al., "In Vitro Maintenance of Highly Purified, Transplantable hematopoietic Stem Cells," Blood 89(12):4337-4347 (1997).
Mooslehner et al., Retroviral Integration Sites in Transgenic Mov Mice Frequently Map in the Vicinity of Transcribed DNA Regions,: J. Virology 64:3056-3058 (1990).
Muchmore et al., "X Ray and NMR Structure of Human Bcl-xL, an Inhibitor of Programmed Cell Death", Nature, vol. 381, May 23, 1996, pp. 335-341.
Non Final Office Action received for U.S. Appl. No. 11/583,970, dated May 9, 2011, 10 pages.
Non Final Office Action received for U.S. Appl. No. 12/048,148, dated Oct. 13, 2011, 9 pages.
Non Final Office Action received for U.S. Appl. No. 12/962,197, dated Aug. 26, 2011, 11 pages.
Non-Final Office Action on U.S. Appl. No. 14/461,105 dated Mar. 22, 2016.
Non-Final Office Action on U.S. Appl. No. 13/797,648 dated Apr. 19, 2018, includes Accession NP 002458.2, 2018.
Non-Final Office Action on U.S. Appl. No. 14/415,325 dated Dec. 23, 2016.
Non-Final Office Action on U.S. Appl. No. 14/461,105 dated Mar. 20, 2017.
Non-Final Office Action on U.S. Appl. No. 14/509,870 dated Jul. 12, 2016.
Non-Final Office Action on U.S. Appl. No. 14/661,786, dated Aug. 27, 2015.
Non-Final Office Action on U.S. Appl. No. 14/873,296 dated Aug. 17, 2017.
Non-Final Office Action on U.S. Appl. No. 15/179,735 dated Feb. 26, 2018.
Non-Final Office Action on U.S. Appl. No. 15/244,138 dated Jan. 22, 2018.
Non-Final Office Action on U.S. Appl. No. 15/785,000 dated Jun. 1, 2018.
Non-Final Office Action on U.S. Appl. No. 12/506,894 dated Apr. 3, 2015, 16 pages.
Non-Final Office Action on U.S. Appl. No. 13/795,659 dated Nov. 26, 2014, 13 pages.
Non-Final Office Action on U.S. Appl. No. 15/643,133 dated Nov. 1, 2019.
Non-Final Office Action on U.S. Appl. No. 15/717,675 dated Feb. 14, 2019.
Non-Final Office Action on U.S. Appl. No. 15/828,971 dated Jul. 8, 2019.
Non-Final Office Action on U.S. Appl. No. 16/042,904 dated Jul. 12, 2019.
Non-Final Office Action on U.S. Appl. No. 16/184,086 dated Feb. 13, 2020.
Non-Final Office Action on U.S. Appl. No. 13/797,648 dated Jun. 17, 2016.
Non-Final Office Action on U.S. Appl. No. 11/583,970 dated Sep. 20, 2013, 19 pages.
Non-final Office Action on U.S. Appl. No. 12/467,957 dated Apr. 4, 2014, 14 pages.
Non-Final Office Action on U.S. Appl. No. 12/701,383 dated Jun. 13, 2014, 26 pages.
Non-final Office Action on U.S. Appl. No. 13/795,659 dated Mar. 10, 2014, 11 pages.
Non-Final Office Action on U.S. Appl. No. 13/797,648 dated Apr. 3, 2014, 14 pages.
Non-Final Office Action received for U.S. Appl. No. 11/583,970, dated Mar. 12, 2008, 13 pages.
Non-Final Office Action received for U.S. Appl. No. 12/467,957 dated Oct. 13, 2010, 15 pages.
Non-Final Office Action received for U.S. Appl. No. 12/701,383, dated Apr. 28, 2011, 9 pages.
Non-Final Office Action received for U.S. Appl. No. 11/583,970, dated Mar. 23, 2009, 11 pages.
Non-Final Office Action received for U.S. Appl. No. 12/048,148 dated Jan. 19, 2011, 6 pages.
Non-Final Office Action received for U.S. Appl. No. 12/048,148, dated May 11, 2012, 9 pages.
Non-Final Office Action received for U.S. Appl. No. 12/506,894, dated Apr. 27, 2012, 13 pages.
Non-Final Office Action received for U.S. Appl. No. 12/550,166 dated Jan. 11, 2012, 7 pages.
Notice of Acceptance issued on Australian Application 2009274172, dated Aug. 3, 2015.
Notice of Acceptance of Australian Application No. 2009246876 dated Apr. 2, 2015, 3 pages.
Notice of Acceptance of Australian Application No. 2012216462, dated Apr. 10, 2015, 2 pages.
Notice of Allowance on U.S. Appl. No. 11/583,970, dated Aug. 29, 2014, 11 pages.
Notice of Allowance on U.S. Appl. No. 12/467,957, dated Nov. 26, 2014, 7 pages.
Notice of Allowance on U.S. Appl. No. 13/795,659 dated Mar. 1, 2016.
Notice of Allowance on U.S. Appl. No. 13/795,659, dated Sep. 29, 2015.
Notice of Allowance on U.S. Appl. No. 14/415,325 dated Jun. 9, 2017.
Notice of Allowance on U.S. Appl. No. 14/461,105 dated Jun. 2, 2017.
Notice of Allowance on U.S. Appl. No. 14/509,870 dated Jun. 22, 2017.
Notice of Allowance on U.S. Appl. No. 14/661,786 dated Apr. 25, 2016.
Notice of Allowance on U.S. Appl. No. 15/179,735 dated May 29, 2018.
Notice of Allowance on U.S. Appl. No. 12/506,894 dated Jun. 16, 2015, 8 pages.
Notice of Allowance on U.S. Appl. No. 12/701,383 dated May 22, 2015, 9 pages.
Notice of Allowance on U.S. Appl. No. 13/777,967 dated Jul. 14, 2014.
Notice of Allowance on U.S. Appl. No. 13/797,648 dated Dec. 6, 2018.
Notice of Allowance on U.S. Appl. No. 15/244,138 dated Jun. 5, 2019.
Notice of Allowance on U.S. Appl. No. 15/668,451 dated Aug. 10, 2018.
Notice of Allowance on U.S. Appl. No. 15/717,675 dated Sep. 17, 2019.
Notice of Allowance on U.S. Appl. No. 15/717,675 dated Nov. 6, 2019.
Notice of Allowance on U.S. Appl. No. 15/785,000 dated Sep. 26, 2018.
Notice of Allowance on U.S. Appl. No. 15/828,971 dated Nov. 1, 2019.
Notice of Allowance on U.S. Appl. No. 16/042,904 dated Dec. 11, 2019.
Notice of Allowance on U.S. Appl. No. 12/550,166 dated Apr. 28, 2014, 4 pages.
Notice of Allowance received for U.S. Appl. No. 12/550,166, dated Nov. 26, 2012, 9 pages.
Notice of Reasons for Rejection (English translation) issued on Japanese application 2014-108137, dated Aug. 18, 2015.
Notice of Reasons for Rejection issued on Japanese Application 2014-108137, dated Nov. 1, 2017.
Notice of Reasons for Rejection issued on Japanese Application 2015-075703, dated Dec. 8, 2016, with English translation.
Notice of Reasons for Rejection issued on Japanese Application 2015-075703, dated May 11, 2016, English translation.
Notice of Reasons for Rejection issued on Japanese application 2015-523297, dated Jul. 19, 2017, English Translation only.
Notice of Reasons for Rejection issued on Japanese Application 2016-027812, dated Mar. 1, 2017.

(56) References Cited

OTHER PUBLICATIONS

Notice of Reasons for Rejection issued on Japanese Application 2016-501113, dated Dec. 28, 2017.
Notice of Reasons for Rejection issued on Japanese Application 2016-501117, dated Apr. 17, 2017.
Notification prior to Allowance of Israeli Patent Application No. 209343 dated Apr. 7, 2014, 2 pages.
Office Action issued Korean Application 10-2010-7028384, dated Mar. 28, 2017, with English Translation.
Office Action issued on Australian Application 2014249202, dated Nov. 18, 2015.
Office Action issued on Canadian Appl. 2626525, dated Jun. 6, 2016.
Office Action issued on Canadian Application 2,626,525 dated Jun. 13, 2017.
Office Action issued on Canadian Application 2723114, dated Jul. 7, 2016.
Office Action issued on Canadian Application 2731767, dated Oct. 5, 2015.
Office Action issued on Canadian Application 2735522, dated Nov. 16, 2015.
Office Action issued on Chinese Application 201410168106.2, dated Jun. 22, 2017 English translation only.
Office Action issued on Chinese Application 201410479865.2, dated Jul. 5, 2016, with English Translation.
Office Action issued on Chinese Application 201480026147.6, dated Apr. 20, 2017, English translation.
Office Action issued on Chinese Application 201480026147.6, dated Sep. 28, 2017.
Office Action issued on Chinese Application 201510760532X, dated May 11, 2018.
Office Action issued on EP Application 09747016.5, dated Jun. 12, 2017.
Office Action issued on Japanese application 2015-523297, dated Apr. 3, 2017.
Office Action issued on Japanese Application 2016-501117, dated Nov. 15, 2017.
Office Action issued on Korean Appl. 10-2010-7028384, dated Aug. 18, 2016 with English translation.
Office Action on Canadian Application No. 2,626,525 dated Apr. 8, 2014, 4 pages.
Office Action on Canadian Application No. 2626525 dated May 8, 2015, 3 pages.
Office Action on Canadian Patent Application No. 2,680,613 dated Nov. 21, 2013, 3 pages.
Office Action on MX/a/2015/012168 dated Aug. 31, 2018.
Office Action received for Australian Patent Application No. 2006304392, dated Jul. 16, 2012, 3 pages.
Office Action received for Australian Patent Application No. 2009246876 dated Jan. 17, 2014, 6 pages.
Office Action received for Australian Patent Application No. 2009285547, dated Jul. 25, 2011, 2 pages.
Office Action received for Canadian Patent Application No. 2626525, dated Apr. 17, 2013, 4 pages.
Office Action received for Canadian Patent Application No. 2731767, dated Jul. 25, 2012, 3 pages.
Office Action received for Canadian Patent Application No. 2735522, dated Sep. 10, 2012, 3 pages.
Office Action received for Chinese Patent Application No. 200580031545.8, dated Jul. 3, 2012, English translation, 11 pages.
Office Action received for Chinese Patent Application No. 200680045545.8, dated Dec. 31, 2010, English translation, 8 pages.
Office Action received for Chinese Patent Application No. 200680045545.8, dated Sep. 15, 2011, English translation, 9 pages.
Office Action received for Chinese Patent Application No. 200880015602.7, dated Jan. 31, 2012, 16 pages (10 pages of English translation and 6 pages of Office Action).
Office Action received for Chinese Patent Application No. 200880015602.7, dated May 9, 2013, 13 pages (8 pages of English Translation and 5 pages of Official copy).
Office Action received for Chinese Patent Application No. 200880015602.7, dated Oct. 31, 2012, 10 pages (6 pages of English Translation and 4 pages of Chinese Office Action).
Office Action received for Chinese Patent Application No. 200980126312.4, dated Aug. 28, 2012, 12 pages (6 pages of English Translation and 6 pages of Office Action).
Office Action received for Chinese Patent Application No. 200980127166.7, dated Dec. 5, 2012, 4 pages (1 page of English Translation and 3 pages of Office Action).
Office Action received for Chinese Patent Application No. 200980126312.4, dated Jan. 30, 2012, 14 pages (7 pages of English translation and 7 pages of Office Action).
Office Action received for European Patent Application No. 06826025.6, dated Sep. 1, 2009, 3 pages.
Office Action received for European Patent Application No. 06826025.6, dated Sep. 22, 2009, 1 page.
Office Action received for European Patent Application No. 08743862.8, dated May 14, 2010, 6 pages.
Office Action received for European Patent Application No. 08743862.8, dated Sep. 23, 2010, 6 pages.
Office Action received for European Patent Application No. 09747016.5, dated Apr. 9, 2013, 6 pages.
Office Action received for European Patent Application No. 09810692.5, dated Mar. 28, 2012, 3 pages.
Office Action received for Indian Application No. 3332/DELNP/2008 dated Aug. 23, 2013, 3 pages.
Office Action received for Israel Patent Application No. 200919, dated Jan. 17, 2013, 4 pages (2 pages of English Translation and 2 pages of Official Copy).
Office Action received for Israel Patent Application No. 208810, dated Nov. 2, 2011, 3 pages of English Translation only.
Office Action received for Israel Patent Application No. 209343, dated Aug. 14, 2012, 3 pages (2 pages of English Translation and 1 page of Office Action).
Office Action received for Israel Patent Application No. 209343, dated Nov. 2, 2011, 3 pages of English Translation only.
Office Action received for Israel Patent Application No. 209968, dated Aug. 21, 2012, 4 pages (2 pages of English Translation and 2 pages of Office Action).
Office Action received for Israel Patent Application No. 209968, dated Nov. 2, 2011, 3 pages of English Translation only.
Office Action received for Israel Patent Application No. 200919, dated Dec. 5, 2011, 2 pages of English Translation only.
Office Action received for Israeli Patent Application No. 190946, dated Jul. 3, 2012, 1 page, (English Translation only).
Office Action received for Israeli Patent Application No. 208810, dated Jan. 2, 2013, 4 pages (English Translation only).
Office Action received for Japanese Application No. 2011-520133, dated Feb. 5, 2014, 4 pages (in Japanese).
Office Action received for Japanese Patent Application No. 2008-536713, dated Jul. 3, 2012, 2 pages (No English Translation Provided).
Office Action received for Japanese Patent Application No. 2009-553785, dated Jun. 19, 2012, 6 pages (2 pages of English Translation and 4 pages of Office Action).
Office Action received for Korean Patent Application No. 10-2008-7011791, dated May 28, 2013, English translation, 3 pages.
Office Action received for Korean Patent Application No. 10-2009-7021320, dated Jul. 29, 2011, 7 pages (3 pages of English Translation and 4 pages of Office Action).
Office Action received for Korean Patent Application No. 10-2009-7021320, dated Sep. 18, 2012, 11 pages (7 pages of English Translation and 4 pages of Office Action).
Official Action on European Application No. 09810692.5 dated Oct. 22, 2014, 3 pages.
Oral Proceedings Summons received for European Patent Application No. 08743862.8, mailed on May 14, 2012, 6 pages.
Pan et al., "Reprogramming human fibroblasts using HIV-1 TAT recombinant proteins OCT4, SOX2, KLF4 and c-MYC," Mol. Biol Rep (2010) 37:2117-2124.
Partial Search Report issued on EP Appl. 14778538.0, dated Jul. 8, 2016.

(56) References Cited

OTHER PUBLICATIONS

Partial Supplementary European Search Report issued on EP Appl. 13820331.0, dated Jun. 30, 2016.
Patel et al., "The c-MYC oncoprotein is a substrate of the acetyltransferases hGCN5/PCAF and TIP60," Molecular and Cellular Biology, Dec. 1, 2004, vol. 24, No. 24, pp. 10826-10834.
PCT/US08/56896 Written Opinion dated Jul. 18, 2008.
Penuela, et al., "Erythropoietin reduces storage lesions and decreases apoptosis indices in blood bank red blood cells", Revista Brasileira de Hematologia e Hemoterapia 38(1): 15-20 (2016).
Pharmaceutics (Yakuzaigaku), 64(3), 2004, p. 164-167 (English translation not available).
Pierelli et al., "Modulation of bcl-2 and p27 in human primitive proliferating hematopoietic progenitors by autocrine TGF-B 1 is a cell cycle-independent effect and influences their hematopoietic potential," Blood 95:3001-3010 (2000).
Pinto et al., "Hematopoietic progenitor/stem cells immortalized by Lhx2 generate functional hematopoietic cells in vivo," Blood 99(11):3939-3946 (2002).
Podsypanina, K. et al., "Oncogene cooperation in tumor maintenance and tumor recurrence in mouse mammary tumors induced by MYC and mutant Kras," PNAS 105(13):5242-5247 (2008).
Polenakovic et al., "Is Erythropoietin a Survival Factor for Red Blood Cells," J. Am. Soc. Nephrol, vol. 7, 1996, pp. 1178-1182.
Pollock, K. et al., "A conditionally immortal clonal stem cell line from human cortical neuroepithelium for the treatment of ischemic stroke," Exp. Neurol., (2006), vol. 199, No. 1, pp. 143-155.
Pre-Appeal Examination Report on Japanese Application 2014-108137, dated Dec. 7, 2016, with English translation.
Prochownik et al., "Deregulated expression of c-myc by murine erythroleukaemia cells prevents differentiation," Nature, vol. 322, Aug. 28, 1986, pp. 848-850.
Qin et al., "Nuclear factor KB Nuclear Translocation Upregulates c-Myc and p53 Expression during NMDA Receptor-Mediated Apoptosis in Rat Striatum", The Journal of Neuroscience, vol. 19, No. 10, May 15, 1999, pp. 4023-4033.
Rabbitts, et al., "Metabolism of c-myc gene products: c-myc mRNA and protein expression in the cell cycle", EMBO Journal, (1985), vol. 4, No. 8, pp. 2009-2015.
Radhakrishnan et al., "A Novel Transcriptional Inhibitor Induces Apoptosis in Tumor Cells and Exhibits Antiangiogenic Activity", Cancer Research, vol. 66, No. 6, Mar. 15, 2006, pp. 3264-3270.
Raymon, H.K. et al., "Immortalized human dorsal root ganglion cells differentiate into neurons with nociceptive properties," J. Neuroscience 19(13):5420-5428 (1999).
Re-Examination Report on Australian Patent No. 2009285547 dated Apr. 23, 2015, 3 pages.
Refaeli, Y, "The B-Cell Antigen Receptor and Overexpression of MYC Can Cooperate in the Genesis of B-Cell Lymphomas", PLOS Biology, vol. 6, No. 6, e152, 2008, pp. 1208-1225.
Request for ReExamination filed in Chinese Patent Application No. 200680045545.8 on Oct. 12, 2012, 17 pages (6 pages of English Machine Translation and 11 pages of Chinese-Language Document as filed).
Restriction Requirement received for U.S. Appl. No. 11/583,970, dated Nov. 13, 2007, 14 pages.
Restriction Requirement received for U.S. Appl. No. 12/701,383, dated Jan. 25, 2011, 10 pages.
Richter, et al., "Lhx.2 expression in hematopoietic progenitor/stem cells in vivo causes a chronic myeloproliferative disorder and altered globin expression," J. Hematol., (2003), 88(12):1336-1347.
Roh et al., "Transgenic Mice for Cre-Inducible Expression of the Oncogenes c-MYC and Pim-1 in Multiple Tissues", Genesis: The Journal of Genetics and Development, vol. 44 pp. 447-453, (2006).
Rosenwald, et al., "Increased Expression of Eukaryotic Translation Inhibition Factors eIF-4E and eIF-2alpha in Response to Growth Induction by C-MYC", Proc. Natl. Acad. Sci. USA, vol. 90, pp. 6175-6178, (1993).

Rubinstein, et al., "Ex Vivo Interleukin-12-Priming During CD8 T Cell Activation Dramatically Improves Adoptive T Cell Transfer Antitumor Efficacy in a Lymphodepleted Host", J. Am. Coll. Surg. 214(4): 700-707 (2002).
Rudolph et al., "Expression of Mad1 in T cells leads to reduced thymic cellularity and impaired mitogen-induced proliferation", Oncogene, 2001, vol. 20, pp. 1164-1175.
Satoh et al, "Roles for c-Myc in Self-renewal of Hematopoietic Stem Cells," The Journal of Biological Chemistry, 2004, vol. 279, No. 24, p. 24986-24993.
Sauer, "Inducible Gene Targeting in Mice Using the Cre/lox System," Methods, (1998), vol. 14, No. 4, pp. 381-392.
Schiedlmeier et al., "High-level Ectopic HOXB4 Expression Confers a Profound in Vivo Competitive Growth Advantage on Human Cord Blood CD34 Cells, but Impairs Lymphomyeloid Differentiation", Blood, vol. 101, No. 5, Mar. 1, 2003, pp. 1759-1768.
Schmidt et al., "Transgenic Mice Bearing the Human c-myc Gene Activated by an Immunoglobulin Enhancer: A pre-B-cell Lymphoma Model", National Academy of Sciences, vol. 85, pp. 6047-6051 (1988).
Schroy, et al., "A Simple Method for Freezing and Thawing Cultured Cells," Methods in Cell Science (formerly known as TCA Manual), (1976), vol. 2, No. 1, pp. 309-310.
Schwarze, et al., "Protein transduction: unrestricted delivery into all cells?" Trends Cell Biol. 10:290-295 (2000).
Schwarze, et al., "In vivo protein transduction: intracellular delivery of biologically active proteins, compounds and DNA," Trends Pharmacol Sci, vol. 21, Feb. 2000, pp. 45-48.
Second Office Action issued on Chinese Application 201480026500.0, dated Apr. 27, 2018.
Seibutsugaku Jiten (Dictionary of Biology), Iwanami Shoten, 1997, The 4th edition, p. 1396, English translation not available.
Siebenlist, et al., "E. coli RNA Polymerase Interacts Homologously with Two Different Promoters," Cell, vol. 20, Jun. 1980, pp. 269-281.
Silva et al., "Erythropoietin Can Promote Erythroid Progenitor Survival by Repressing Apoptosis Through Bcl-xl, and Bcl-2," Blood 88(5): 1576-1582 (1996).
Sipione, S. et al., "Modeling brain pathologies using neural stem cells," Methods Mol. Biol., (2002), vol. 198, pp. 245-262.
Snyder, et al., "Regulation of NMDA receptor trafficking by amyloid-3B2", Nature Neuroscience, (2005), vol. 8, No. 8, pp. 1051-1058.
Soane,L., et al., "TAT-mediated endocytotic delivery of the loop deletion Bcl-2 protein protects neurons against cell death", Journal of Neurochemistry, (2005), vol. 95, pp. 230-243.
Song, "Cloning and expression of PTD-BDNF fusion gene and purification of expressed product", Bioengineering Pharmaceutical Research and Practice, Anhui Science and Technology Press, 1st Ed., pp. 200-201 (Feb. 2009).
Stein et al., "TAT-MYC Recombinant Fusion Protein Enhances Hematopoietic Stem Cell Graft Performance and Immunne Cell Reconstitution after Transplantation," Blood, Dec. 7, 2017, vol. 130, Suppl. 1, p. 3175.
Sunyer, "Evolutionary and Functional Relationships of B Cells from Fish and Mammals: Insights into their Novel Roles in Phagocytosis and Presentation of Particulate Antigen," Infect Disord Drug Targets 12(3):200-212 (2012).
Supplementary Search Report received for European Patent Application No. 06826025.6, dated Aug. 13, 2009.
Supplementary Search Report received for European Patent Application No. 08743862.8 dated Feb. 9, 2010, 1 page.
Taguchi et al., "Nuclear trafficking of macromolecules by an oligopeptide derived from Vpr of human immunodeficiency virus type-1" Biochem. Biophys. Res. Commun. 2004, 320(1) pp. 18-26.
Takahashi, et al., Induction of pluripotent stem cells from mouse embryonic and adult fibroblast cultures by defined factors, Cell, 126:663-676, 2006.
Theis, et al., "Expression of the myc/His-Tagged Human Peptide Transporter hPEPT1 in Yeast for Protein Purification and Functional Analysis", Protein Expression and Purification, (2001), vol. 22, pp. 436-442.

(56) References Cited

OTHER PUBLICATIONS

Thomas, et. al., "Progress and Problems with the Use of Viral Vectors for Gene Therapy", Nature, (May 2003), vol. 4, pp. 346-358.

Trumpp et al., "c-Myc Regulates Mammalian Body Size by Controlling Cell Number But Not Cell Size," Nature 414: 768-773 (2001).

Tsai et al., "Lymphohematopoietic progenitors immortalized by a retroviral vector harboring a dominant-negative retinoic acid receptor can recapitulate lymphoid, myeloid, and erythroid development," Genes & Dev. 8:2831-2841 (1994).

U.S. Appl. No. 12/048,148, filed Mar. 13, 2008.

U.S. Appl. No. 12/506,894, filed Jul. 21, 2009.

Varnum-Finney et al., "Pluripotent, cytokine-dependent, hematopoietic stem cells are immortalized by constitutive Notch1 signaling," Nature Medicine 6(11):1278-1281 (2000).

Vaux et al., "Bcl-2 gene promotes hemopoietic cell survival and cooperates with c-myc to immortalize pre-B cells," Nature 335:440-442 (1988).

Vaux, et al., "Immunologic competence of B cells subjected to constitutive c-myc oncogene expression in immunoglobulin heavy chain enhancer myc transgenic mice", J. Immunol., (1987), vol. 139, No. 11, pp. 3854-3860.

Wagner et al., "Myc-Mediated Apoptosis is Blocked by Ectopic Expression of Bcl-2," Molecular and Cellular Biology, Apr. 1993, pp. 2432-2440.

Wang et al., "Primitive Human Hematopoietic Cells Are Enriched in Cord Blood Compared with Adult Bone Marrow or Mobilized Peripheral Blood as Measured by the Quantitative In Vivo SCID-Repopulating Cell Assay," Blood 89:3919-3924 (1997).

Wang, "Instability, stabilization, and formulation of liquid protein pharmaceuticals," Int. J. Pharm., vol. 185, Issue 2, Aug. 20, 1999, pp. 129-188.

Wang, "Lyophilization and development of solid protein pharmaceuticals," Int. J. Pharm., vol. 203, Issues 1-2, Aug. 2000, pp. 1-60.

Watt, et al., "Nucleotide sequence of cloned cDNA of human c-myc oncogene", Nature 303: 725-728 (1983).

Wechsler et al., "MXI1, a Putative Tumor Suppressor Gene, Suppresses Growth of Human Glioblastoma Cells", Cancer Research 57, pp. 4405-4912, (1997).

Wikipedia [online], "Stem Cell", 2008, [retrieved on Nov. 13, 2008]. Retrieved from the Internet: <URL: http//en.wikipedia.org/wiki/Stem_cell>, 11 pages.

Wilson, et al., "c-Myc controls the balance between hematopoietic stem cell self-renewal and differentiation", Genes and Development 18: 2747-2763(2004).

Wu et al., "Inhibition of c-myc Expression Induces Apoptosis of WEHI 231 Murine B Cells", Molecular and Cellular Biology, Sep. 1996, vol. 16, No. 9, pp. 5015-5025.

Wurm, et al., "Large-scale transient expression of mammalian cells for recombinant protein production," Curr. Op. Biotech., (1999), vol. 10, pp. 156-159.

Xi et al., "In Vitro Large Scale Production of Human Mature Red Blood Cells From Hematopoietic Stem Cells by Cocuituring with Human Fetal Liver Stromal Cells," Biomed. Res. Int. Epub Jan. 30, 2013, 2013:807863.

Xi, et al., Biomed. Res. Int. Epub 2013: 807863 (Jan. 30, 2013).

Xu Zhixiang, et al, "The Development of the Study on the Anti-Tumor Effect of Flt3 Ligand," Chinese Journal of Tumor Biological Therapy, vol. 7, No. 3, Sep. 30, 2000.

Yagihashi, et al., "Detection of Anti-Survivin Antibody in Gastrointestinal Cancer Patients", Clinical Chemistry, (2001), vol. 47, No. 9, pp. 1729-1731.

Yanai et al., "A novel stromal cell-dependent hematopoietic cell line established from temperature-sensitive SV40 T-antigen transgenic mice," Exp. Hematol., 27:1087-1096 (1999).

Young et al., "B-Cell Receptor Signaling in the Genesis and Maintenance of B-Cell Lymphoma", Future Oncology, vol. 4, No. 5, 2008, pp. 591-594.

Zhang et al., "Cytokines Regulating Hematopoietic Stem Cell Function", Current Opinion Hematology, vol. 15, No. 4, Jul. 2008, pp. 307-311.

Zhang et al., "Reprogramming of somatic cells via TAT-mediated protein transduction of recombinant factors," Biomaterials 33 (2012) 5047-5055.

Office Action on JP 2019-025374 dated Mar. 9, 2020.

Office Action on JP 2018-153567 dated Mar. 18, 2020.

Notice of Allowance on U.S. Appl. No. 16/042,904 dated Mar. 20, 2020.

Canadian Office Action on CA 2879667 dated May 25, 2020.

Japanese Office Action on JP 2019-512193 dated May 13, 2020.

McNiece, et al, "Ex-vivo expansion of hematopoietic progenitor cells: preliminary results in breast cancer", Hematol. Cell Ther. 41(2): 82-86 (1999).

Non-Final Office Action on U.S. Appl. No. 16/261,207 dated May 13, 2020.

Notice of Allowance on U.S. Appl. No. 15/643,133 dated May 15, 2020.

Zhuang, et al., "C-MYC overexpression is required for continuous suppression of oncogene-induced senescence in melanoma cells", Oncogene 27: 6623-6634 (2008).

Office Action on JP 2019-529651 dated Jul. 15, 2020.

International Search Report and Written Opinion on PCT/US2020/027070 dated Sep. 18, 2020.

\* cited by examiner

SEQUENCE LISTING

```
<160> NUMBER OF SEQ ID NOS: 13

<210> SEQ ID NO 1
<211> LENGTH: 476
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Arg Lys Lys Arg Arg Gln Arg Arg Pro Leu Asn Val Ser Phe
1               5                   10                  15

Thr Asn Arg Asn Tyr Asp Leu Asp Tyr Asp Ser Val Gln Pro Tyr Phe
                20                  25                  30

Tyr Cys Asp Glu Glu Glu Asn Phe Tyr Gln Gln Gln Gln Ser Glu
            35                  40                  45

Leu Gln Pro Pro Ala Pro Ser Glu Asp Ile Trp Lys Lys Phe Glu Leu
    50                  55                  60

Leu Pro Thr Pro Pro Leu Ser Pro Ser Arg Arg Ser Gly Leu Cys Ser
65                  70                  75                  80

Pro Ser Tyr Val Ala Val Thr Pro Phe Ser Leu Arg Gly Asp Asn Asp
                85                  90                  95

Gly Gly Gly Gly Ser Phe Ser Thr Ala Asp Gln Leu Glu Met Val Thr
            100                 105                 110

Glu Leu Leu Gly Gly Asp Met Val Asn Gln Ser Phe Ile Cys Asp Pro
        115                 120                 125

Asp Asp Glu Thr Phe Ile Lys Asn Ile Ile Ile Gln Asp Cys Met Trp
    130                 135                 140

Ser Gly Phe Ser Ala Ala Ala Lys Leu Val Ser Glu Lys Leu Ala Ser
145                 150                 155                 160

Tyr Gln Ala Ala Arg Lys Asp Ser Gly Ser Pro Asn Pro Ala Arg Gly
                165                 170                 175

His Ser Val Cys Ser Thr Ser Ser Leu Tyr Leu Gln Asp Leu Ser Ala
            180                 185                 190

Ala Ala Ser Glu Cys Ile Asp Pro Ser Val Val Phe Pro Tyr Pro Leu
        195                 200                 205

Asn Asp Ser Ser Ser Pro Lys Ser Cys Ala Ser Gln Asp Ser Ser Ala
    210                 215                 220

Phe Ser Pro Ser Ser Asp Ser Leu Leu Ser Ser Thr Glu Ser Ser Pro
225                 230                 235                 240

Gln Gly Ser Pro Glu Pro Leu Val Leu His Glu Glu Thr Pro Pro Thr
                245                 250                 255
```

-continued

```
Thr Ser Ser Asp Ser Glu Glu Glu Gln Glu Asp Glu Glu Ile Asp
            260                 265                 270

Val Val Ser Val Glu Lys Arg Gln Ala Pro Gly Lys Arg Ser Glu Ser
        275                 280                 285

Gly Ser Pro Ser Ala Gly Gly His Ser Lys Pro Pro His Ser Pro Leu
    290                 295                 300

Val Leu Lys Arg Cys His Val Ser Thr His Gln His Asn Tyr Ala Ala
305                 310                 315                 320

Pro Pro Ser Thr Arg Lys Asp Tyr Pro Ala Ala Lys Arg Val Lys Leu
                325                 330                 335

Asp Ser Val Arg Val Leu Arg Gln Ile Ser Asn Asn Arg Lys Cys Thr
            340                 345                 350

Ser Pro Arg Ser Ser Asp Thr Glu Glu Asn Val Lys Arg Arg Thr His
        355                 360                 365

Asn Val Leu Glu Arg Gln Arg Arg Asn Glu Leu Lys Arg Ser Phe Phe
    370                 375                 380

Ala Leu Arg Asp Gln Ile Pro Glu Leu Glu Asn Asn Glu Lys Ala Pro
385                 390                 395                 400

Lys Val Val Ile Leu Lys Lys Ala Thr Ala Tyr Ile Leu Ser Val Gln
                405                 410                 415

Ala Glu Glu Gln Lys Leu Ile Ser Glu Glu Asp Leu Leu Arg Lys Arg
            420                 425                 430

Arg Glu Gln Leu Lys His Lys Leu Glu Gln Leu Arg Lys Gly Glu Leu
        435                 440                 445

Asn Ser Lys Leu Glu Gly Lys Pro Ile Pro Asn Pro Leu Leu Gly Leu
    450                 455                 460

Asp Ser Thr Arg Thr Gly His His His His His His
465                 470                 475

<210> SEQ ID NO 2
<211> LENGTH: 439
<212> TYPE: PRT
<213> ORGANISM: Homo sapiens

<400> SEQUENCE: 2

Met Pro Leu Asn Val Ser Phe Thr Asn Arg Asn Tyr Asp Leu Asp Tyr
1               5                   10                  15

Asp Ser Val Gln Pro Tyr Phe Tyr Cys Asp Glu Glu Glu Asn Phe Tyr
            20                  25                  30

Gln Gln Gln Gln Gln Ser Glu Leu Gln Pro Pro Ala Pro Ser Glu Asp
        35                  40                  45

Ile Trp Lys Lys Phe Glu Leu Leu Pro Thr Pro Pro Leu Ser Pro Ser
    50                  55                  60

Arg Arg Ser Gly Leu Cys Ser Pro Ser Tyr Val Ala Val Thr Pro Phe
65                  70                  75                  80

Ser Leu Arg Gly Asp Asn Asp Gly Gly Gly Gly Ser Phe Ser Thr Ala
                85                  90                  95

Asp Gln Leu Glu Met Val Thr Glu Leu Leu Gly Gly Asp Met Val Asn
            100                 105                 110

Gln Ser Phe Ile Cys Asp Pro Asp Asp Glu Thr Phe Ile Lys Asn Ile
        115                 120                 125

Ile Ile Gln Asp Cys Met Trp Ser Gly Phe Ser Ala Ala Ala Lys Leu
    130                 135                 140

Val Ser Glu Lys Leu Ala Ser Tyr Gln Ala Ala Arg Lys Asp Ser Gly
```

```
            145                 150                 155                 160
Ser Pro Asn Pro Ala Arg Gly His Ser Val Cys Ser Thr Ser Ser Leu
                    165                 170                 175

Tyr Leu Gln Asp Leu Ser Ala Ala Ser Glu Cys Ile Asp Pro Ser
                180                 185                 190

Val Val Phe Pro Tyr Pro Leu Asn Asp Ser Ser Pro Lys Ser Cys
            195                 200                 205

Ala Ser Gln Asp Ser Ser Ala Phe Ser Pro Ser Ser Asp Ser Leu Leu
        210                 215                 220

Ser Ser Thr Glu Ser Ser Pro Gln Gly Ser Pro Glu Pro Leu Val Leu
225                 230                 235                 240

His Glu Glu Thr Pro Pro Thr Thr Ser Ser Asp Ser Glu Glu Glu Gln
                245                 250                 255

Glu Asp Glu Glu Glu Ile Asp Val Val Ser Val Glu Lys Arg Gln Ala
                260                 265                 270

Pro Gly Lys Arg Ser Glu Ser Gly Ser Pro Ser Ala Gly Gly His Ser
                275                 280                 285

Lys Pro Pro His Ser Pro Leu Val Leu Lys Arg Cys His Val Ser Thr
        290                 295                 300

His Gln His Asn Tyr Ala Ala Pro Pro Ser Thr Arg Lys Asp Tyr Pro
305                 310                 315                 320

Ala Ala Lys Arg Val Lys Leu Asp Ser Val Arg Val Leu Arg Gln Ile
                325                 330                 335

Ser Asn Asn Arg Lys Cys Thr Ser Pro Arg Ser Ser Asp Thr Glu Glu
                340                 345                 350

Asn Val Lys Arg Arg Thr His Asn Val Leu Glu Arg Gln Arg Arg Asn
                355                 360                 365

Glu Leu Lys Arg Ser Phe Phe Ala Leu Arg Asp Gln Ile Pro Glu Leu
                370                 375                 380

Glu Asn Asn Glu Lys Ala Pro Lys Val Val Ile Leu Lys Lys Ala Thr
385                 390                 395                 400

Ala Tyr Ile Leu Ser Val Gln Ala Glu Glu Gln Lys Leu Ile Ser Glu
                405                 410                 415

Glu Asp Leu Leu Arg Lys Arg Arg Glu Gln Leu Lys His Lys Leu Glu
                420                 425                 430

Gln Leu Arg Asn Ser Cys Ala
            435

<210> SEQ ID NO 3
<211> LENGTH: 450
<212> TYPE: PRT
<213> ORGANISM: Homo sapiens

<400> SEQUENCE: 3

Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
                20                  25                  30

Ser Val Gln Pro Tyr Phe Tyr Cys Asp Glu Glu Glu Asn Phe Tyr Gln
            35                  40                  45

Gln Gln Gln Gln Ser Glu Leu Gln Pro Pro Ala Pro Ser Glu Asp Ile
        50                  55                  60

Trp Lys Lys Phe Glu Leu Leu Pro Thr Pro Pro Leu Ser Pro Ser Arg
65                  70                  75                  80
```

Arg Ser Gly Leu Cys Ser Pro Ser Tyr Val Ala Val Thr Pro Phe Ser
              85                  90                  95

Leu Arg Gly Asp Asn Asp Gly Gly Gly Ser Phe Ser Thr Ala Asp
        100                 105                 110

Gln Leu Glu Met Val Thr Glu Leu Leu Gly Gly Asp Met Val Asn Gln
        115                 120                 125

Ser Phe Ile Cys Asp Pro Asp Glu Thr Phe Ile Lys Asn Ile Ile
        130                 135                 140

Ile Gln Asp Cys Met Trp Ser Gly Phe Ser Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190

Leu Gln Asp Leu Ser Ala Ala Ala Ser Glu Cys Ile Asp Pro Ser Val
            195                 200                 205

Val Phe Pro Tyr Pro Leu Asn Asp Ser Ser Pro Lys Ser Cys Ala
        210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Glu Gln Glu
                260                 265                 270

Asp Glu Glu Glu Ile Asp Val Val Ser Val Glu Lys Arg Gln Ala Pro
            275                 280                 285

Gly Lys Arg Ser Glu Ser Gly Ser Pro Ser Ala Gly Gly His Ser Lys
        290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
        355                 360                 365

Val Lys Arg Arg Thr His Asn Val Leu Glu Arg Gln Arg Arg Asn Glu
        370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
            420                 425                 430

Asp Leu Leu Arg Lys Arg Arg Glu Gln Leu Lys His Lys Leu Glu Gln
        435                 440                 445

Leu Arg
    450

<210> SEQ ID NO 4
<211> LENGTH: 434
<212> TYPE: PRT
<213> ORGANISM: Homo sapiens

<400> SEQUENCE: 4

-continued

```
Pro Leu Asn Val Ser Phe Thr Asn Arg Asn Tyr Asp Leu Asp Tyr Asp
1               5                   10                  15
Ser Val Gln Pro Tyr Phe Tyr Cys Asp Glu Glu Asn Phe Tyr Gln
            20                  25                  30
Gln Gln Gln Gln Ser Glu Leu Gln Pro Pro Ala Pro Ser Glu Asp Ile
        35                  40                  45
Trp Lys Lys Phe Glu Leu Leu Pro Thr Pro Pro Leu Ser Pro Ser Arg
    50                  55                  60
Arg Ser Gly Leu Cys Ser Pro Ser Tyr Val Ala Val Thr Pro Phe Ser
65                  70                  75                  80
Leu Arg Gly Asp Asn Asp Gly Gly Gly Ser Phe Ser Thr Ala Asp
                85                  90                  95
Gln Leu Glu Met Val Thr Glu Leu Leu Gly Gly Asp Met Val Asn Gln
            100                 105                 110
Ser Phe Ile Cys Asp Pro Asp Asp Glu Thr Phe Ile Lys Asn Ile Ile
        115                 120                 125
Ile Gln Asp Cys Met Trp Ser Gly Phe Ser Ala Ala Ala Lys Leu Val
    130                 135                 140
Ser Glu Lys Leu Ala Ser Tyr Gln Ala Ala Arg Lys Asp Ser Gly Ser
145                 150                 155                 160
Pro Asn Pro Ala Arg Gly His Ser Val Cys Ser Thr Ser Ser Leu Tyr
                165                 170                 175
Leu Gln Asp Leu Ser Ala Ala Ala Ser Glu Cys Ile Asp Pro Ser Val
            180                 185                 190
Val Phe Pro Tyr Pro Leu Asn Asp Ser Ser Pro Lys Ser Cys Ala
        195                 200                 205
Ser Gln Asp Ser Ser Ala Phe Ser Pro Ser Ser Asp Ser Leu Leu Ser
    210                 215                 220
Ser Thr Glu Ser Ser Pro Gln Gly Ser Pro Glu Pro Leu Val Leu His
225                 230                 235                 240
Glu Glu Thr Pro Pro Thr Thr Ser Ser Asp Ser Glu Glu Glu Gln Glu
                245                 250                 255
Asp Glu Glu Glu Ile Asp Val Val Ser Val Glu Lys Arg Gln Ala Pro
            260                 265                 270
Gly Lys Arg Ser Glu Ser Gly Ser Pro Ser Ala Gly Gly His Ser Lys
        275                 280                 285
Pro Pro His Ser Pro Leu Val Leu Lys Arg Cys His Val Ser Thr His
    290                 295                 300
Gln His Asn Tyr Ala Ala Pro Pro Ser Thr Arg Lys Asp Tyr Pro Ala
305                 310                 315                 320
Ala Lys Arg Val Lys Leu Asp Ser Val Arg Val Leu Arg Gln Ile Ser
                325                 330                 335
Asn Asn Arg Lys Cys Thr Ser Pro Arg Ser Ser Asp Thr Glu Glu Asn
            340                 345                 350
Val Lys Arg Arg Thr His Asn Val Leu Glu Arg Gln Arg Arg Asn Glu
        355                 360                 365
Leu Lys Arg Ser Phe Phe Ala Leu Arg Asp Gln Ile Pro Glu Leu Glu
    370                 375                 380
Asn Asn Glu Lys Ala Pro Lys Val Val Ile Leu Lys Lys Ala Thr Ala
385                 390                 395                 400
Tyr Ile Leu Ser Val Gln Ala Glu Glu Gln Lys Leu Ile Ser Glu Glu
                405                 410                 415
```

-continued

Asp Leu Leu Arg Lys Arg Arg Glu Gln Leu Lys His Lys Leu Glu Gln
            420                 425                 430

Leu Arg

<210> SEQ ID NO 5
<211> LENGTH: 67
<212> TYPE: PRT
<213> ORGANISM: Homo sapiens

<400> SEQUENCE: 5

Glu Leu Lys Arg Ser Phe Phe Ala Leu Arg Asp Gln Ile Pro Glu Leu
1               5                   10                  15

Glu Asn Asn Glu Lys Ala Pro Lys Val Val Ile Leu Lys Lys Ala Thr
            20                  25                  30

Ala Tyr Ile Leu Ser Val Gln Ala Glu Glu Gln Lys Leu Ile Ser Glu
        35                  40                  45

Glu Asp Leu Leu Arg Lys Arg Arg Glu Gln Leu Lys His Lys Leu Glu
    50                  55                  60

Gln Leu Arg
65

<210> SEQ ID NO 6
<211> LENGTH: 14
<212> TYPE: PRT
<213> ORGANISM: Unknown
<220> FEATURE:
<223> OTHER INFORMATION: Description of Unknown:
      E-box DNA binding domain sequence

<400> SEQUENCE: 6

Lys Arg Arg Thr His Asn Val Leu Glu Arg Gln Arg Arg Asn
1               5                   10

<210> SEQ ID NO 7
<211> LENGTH: 10
<212> TYPE: PRT
<213> ORGANISM: Human immunodeficiency virus 1

<400> SEQUENCE: 7

Met Arg Lys Lys Arg Arg Gln Arg Arg Arg
1               5                   10

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 8

His His His His His His
1               5

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Lys Pro Ile Pro Asn Pro Leu Leu Gly Leu Asp Ser Thr

```
<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ile Pro Asn Pro Leu Leu Gly Leu Asp
1               5

<210> SEQ ID NO 11
<211> LENGTH: 454
<212> TYPE: PRT
<213> ORGANISM: Homo sapiens

<400> SEQUENCE: 11

Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
            20                  25                  30

Ser Val Gln Pro Tyr Phe Tyr Cys Asp Glu Glu Glu Asn Phe Tyr Gln
        35                  40                  45

Gln Gln Gln Gln Ser Glu Leu Gln Pro Pro Ala Pro Ser Glu Asp Ile
    50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Ser Phe Ser Thr Ala Asp
            100                 105                 110

Gln Leu Glu Met Val Thr Glu Leu Leu Gly Gly Asp Met Val Asn Gln
        115                 120                 125

Ser Phe Ile Cys Asp Pro Asp Asp Glu Thr Phe Ile Lys Asn Ile Ile
    130                 135                 140

Ile Gln Asp Cys Met Trp Ser Gly Phe Ser Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190

Leu Gln Asp Leu Ser Ala Ala Ala Ser Glu Cys Ile Asp Pro Ser Val
        195                 200                 205

Val Phe Pro Tyr Pro Leu Asn Asp Ser Ser Ser Pro Lys Ser Cys Ala
    210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Gln Glu
            260                 265                 270

Asp Glu Glu Glu Ile Asp Val Val Ser Val Glu Lys Arg Gln Ala Pro
        275                 280                 285

Gly Lys Arg Ser Glu Ser Gly Ser Pro Ser Ala Gly Gly His Ser Lys
```

```
                290                 295                 300
Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
                340                 345                 350

Asn Asn Arg Lys Cys Thr Ser Pro Arg Ser Ser Asp Thr Glu Glu Asn
                355                 360                 365

Val Lys Arg Arg Thr His Asn Val Leu Glu Arg Gln Arg Arg Asn Glu
                370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
                420                 425                 430

Asp Leu Leu Arg Lys Arg Arg Glu Gln Leu Lys His Lys Leu Glu Gln
                435                 440                 445

Leu Arg Asn Ser Cys Ala
    450

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Gly Glu Leu Asn Ser Lys Leu Glu
1               5

<210> SEQ ID NO 13
<211> LENGTH: 9
<212> TYPE: PRT
<213> ORGANISM: Human immunodeficiency virus 1

<400> SEQUENCE: 13

Arg Lys Lys Arg Arg Gln Arg Arg Arg
1               5
```

METHODS AND COMPOSITIONS FOR THE TREATMENT OF MELANOMA

RELATED APPLICATIONS

The present application is a divisional of U.S. patent application Ser. No. 15/668,451, filed on Aug. 3, 2017, which is related to PCT Application No. PCT/US2017/045336, filed on Aug. 3, 2017, entitled "METHODS AND COMPOSITIONS FOR THE TREATMENT OF MELANOMA". Each of the above-referenced applications is hereby incorporated by reference into the present application in their entirety.

SEQUENCE LISTING

The instant application contains a Sequence Listing, which has been submitted electronically in ASCII format and is hereby incorporated by reference in its entirety. Said ASCII copy, created on Nov. 8, 2018, is named 106417-0431_Sequence_Listing.txt and is 21,978 bytes in size.

BACKGROUND OF THE INVENTION

Adoptive cell transfer (ACT) is a form of immunotherapy that involves the transfer of immune cells with antitumor activity into patients. ACT typically involves isolation of lymphocytes with antitumor activity from a patient, culturing the lymphocytes in vitro to expand the population, and then infusing the lymphocytes into the cancer-bearing host. Lymphocytes used for adoptive transfer can either be derived from the stroma of resected tumors (e.g., tumor infiltrating lymphocytes), from the lymphatics or lymph nodes, or from the blood. In some cases, the isolated lymphocytes are genetically engineered to express antitumor T cell receptors (TCRs) or chimeric antigen receptors (CARs). The lymphocytes used for infusion can be isolated from a donor (allogeneic ACT), or from the cancer-bearing host (autologous ACT).

SUMMARY OF THE INVENTION

Provided herein, in certain embodiments, are methods for adoptive cell transfer for the treatment of melanoma. In some embodiments, provided are methods for the treatment of melanoma in a subject comprising administering a therapeutically effective amount of immune cells having antitumor activity to the subject, wherein the immune cells are contacted with a protein transduction domain (PTD)-MYC fusion polypeptide prior to administration to the subject. In some embodiments, the immune cells comprise one or more lymphocytes. In some embodiments, the one or more lymphocytes comprise T cells and/or B cells. In some embodiments, the one or more lymphocytes comprise tumor-infiltrating lymphocytes. In some embodiments, the melanoma is a metastatic melanoma. In some embodiments, the melanoma is a superficial spreading melanoma, a nodular melanoma, a lentigo maligna melanoma, or an acral melanoma. In some embodiments, the immune cells are obtained from a donor subject having melanoma. In some embodiments, donor subject and the subject receiving the immune cells are the same (i.e., autologous ACT). In some embodiments, donor subject and the subject receiving the immune cells are different (i.e., allogeneic ACT).

In some embodiments, the PTD-MYC fusion polypeptide comprises: (i) an HIV TAT protein transduction domain; and (ii) a MYC polypeptide sequence. In some embodiments, the PTD-MYC fusion polypeptide translocates to the nucleus of the immune cell. In some embodiments, the PTD-MYC fusion polypeptide exhibits a biological activity of MYC, such as the activation of MYC target genes. In some embodiments, the fusion peptide comprises SEQ ID NO: 1.

Described herein, in certain embodiments are compositions comprising (a) a MYC fusion peptide, comprising (i) a protein transduction domain; (ii) a MYC polypeptide sequence; and (b) one or more primary immune cells isolated from a donor subject that has a melanoma tumor, wherein the one or more primary immune cells are reactive against a melanoma-specific antigen. In some embodiments, the MYC fusion peptide translocates to the nucleus of the one or more primary immune cells. In some embodiments, the MYC fusion peptide exhibits a biological activity of MYC. In some embodiments, the MYC fusion peptide further comprises one or more molecules that link the protein transduction domain and the MYC polypeptide. In some embodiments, the MYC fusion peptide comprises a MYC fusion peptide with the following general structure:

protein transduction domain-X-MYC sequence, wherein -X- is molecule that links the protein transduction domain and the MYC sequence. In some embodiments, the protein transduction domain sequence is a TAT protein transduction domain sequence. In some embodiments, the TAT protein transduction domain sequence is selected from the group consisting of TAT[48-57] and TAT[57-48]. In some embodiments, the MYC fusion peptide comprises SEQ ID NO: 1. In some embodiments, the MYC fusion peptide is acetylated. In some embodiments, the one or more immune cells have antitumor activity against melanoma cells. In some embodiments, the one or more immune cells comprises one or more lymphocytes. In some embodiments, the one or more lymphocytes comprises a T cell, a B cell, an NK cell, or any combination thereof. In some embodiments, the T cell is selected from the group consisting of naïve T cells, CD4+ T cells, CD8+ T cells, memory T cells, activated T cells, anergic T cells, tolerant T cells, chimeric T cells, and antigen-specific T cells. In some embodiments, the B cells are selected from the group consisting of naïve B cells, plasma B cells, activated B cells, memory B cells, anergic B cells, tolerant B cells, chimeric B cells, and antigen-specific B cells. In some embodiments, the one or more lymphocytes is a tumor-infiltrating lymphocyte, T-cell receptor modified lymphocyte, or a chimeric antigen receptor modified lymphocyte. In some embodiments, the tumor-infiltrating lymphocyte has a CD8+CD25+ signature. In some embodiments, the tumor-infiltrating lymphocyte has a CD4+CD25+ signature. In some embodiments, the one or more immune cells comprises a detectable moiety.

Described herein, in certain embodiments are methods for treating a melanoma in a subject, comprising administering one or more modified immune cells to the subject in need thereof, wherein the one or more modified immune cells comprise a MYC fusion peptide comprising (i) a protein transduction domain; (ii) a MYC polypeptide sequence and are reactive to a tumor-specific antigen. In some embodiments, the one or more modified immune cells are derived from primary immune cells isolated from the subject. In some embodiments, the one or more modified immune cells are derived from primary immune cells isolated from a separate donor subject having the same type of melanoma. In some embodiments, the one or more modified immune cells are prepared by contacting the primary immune cells in vitro with the MYC fusion peptide following isolation. In some embodiments, the methods further comprise expanding the primary immune cells in vitro prior to contacting with the MYC fusion peptide. In some embodiments, the methods further comprise expanding the primary immune cells following contacting with the MYC fusion peptide. In some embodiments, the cells are expanded using an anti-CD3 antibody. In some embodiments, the cells are expanded using an irradiated allogenic feeder cells. In some embodiments, the cells are expanded in the presence of an exogenous cytokine. In some embodiments, the cytokine is interleukin-2. In some embodiments, the MYC fusion peptide translocates to the nucleus of the immune cell. In some embodiments, the MYC fusion peptide exhibits a biological activity of MYC. In some embodiments, the MYC fusion peptide further comprises one or more molecules that link the protein transduction domain and the MYC polypeptide. In some embodiments, the MYC fusion peptide comprises a MYC fusion peptide with the following general structure:

protein transduction domain-X-MYC sequence, wherein -X- is molecule that links the protein transduction domain and the MYC sequence. In some embodiments, the protein transduction domain sequence is a TAT protein transduction domain sequence. In some embodiments, the TAT protein transduction domain sequence is selected from the group consisting of TAT[48-57] and TAT[57-48]. In some embodiments, the MYC fusion peptide comprises SEQ ID NO: 1. In some embodiments, the MYC fusion peptide is acetylated. In some embodiments, the one or more modified immune cells have antitumor activity against melanoma cells in the subject. In some embodiments, the one or more modified immune cells have antitumor activity against melanoma cells in the subject. In some embodiments, the one or more modified immune cells comprise one or more anergic immune cells. In some embodiments, the one or more immune cells comprises one or more lymphocytes. In some embodiments, the one or more lymphocytes comprises a T cell, a B cell, an NK, or any combination thereof. In some embodiments, the T cell is selected from the group consisting of naïve T cells, CD4+ T cells, CD8+ T cells, memory T cells, activated T cells, anergic T cells, tolerant T cells, chimeric T cells, and antigen-specific T cells. In some embodiments, the B cells are selected from the group consisting of naïve B cells, plasma B cells, activated B cells, memory B cells, anergic B cells, tolerant B cells, chimeric B cells, and antigen-specific B cells. In some embodiments, the one or more lymphocytes is a tumor-infiltrating lymphocyte, T-cell receptor modified lymphocyte, or a chimeric antigen receptor modified lymphocyte. In some embodiments, the lymphocyte has a CD8+CD28−CD152− signature. In some embodiments, the lymphocyte has a CD8+CD25+ signature. In some embodiments, the lymphocyte has a CD4+CD25+ signature. In some embodiments, the methods further comprise isolating the primary immune cells from the donor subject. In some embodiments, the donor subject has melanoma. In some embodiments, the one or more modified immune cells are administered intravenously, intraperitoneally, subcutaneously, intramuscularly, or intratumorally. In some embodiments, the methods further comprise lymphodepleting the subject prior to administration of the one or more modified immune cells. In some embodiments, the methods further comprise administering a cytokine to the subject. In some embodiments, the cytokine is administered prior to, during, or subsequent to administration of the one or more modified immune cells. In some embodiments, the cytokine is selected from a group consisting of interferon α, interferon β, interferon γ, complement C5a, IL-2, TNFalpha, CD40L, IL12, IL-23, IL15, IL17, CCL1, CCL11, CCL12, CCL13, CCL14-1, CCL14-2, CCL14-3, CCL15-1, CCL15-2, CCL16, CCL17, CCL18, CCL19, CCL19, CCL2, CCL20, CCL21, CCL22, CCL23-1, CCL23-2, CCL24, CCL25-1, CCL25-2, CCL26, CCL27, CCL28, CCL3, CCL3L1, CCL4, CCL4L1, CCL5, CCL6, CCL7, CCL8, CCL9, CCR10, CCR2, CCR5, CCR6, CCR7, CCR8, CCRL1, CCRL2, CX3CL1, CX3CR, CXCL1, CXCL10, CXCL11, CXCL12, CXCL13, CXCL14, CXCL15, CXCL16, CXCL2, CXCL3, CXCL4, CXCL5, CXCL6, CXCL7, CXCL8, CXCL9, CXCL9, CXCR1, CXCR2, CXCR4, CXCR5, CXCR6, CXCR7 and XCL2. In some embodiments, the melanoma is metastatic. In some embodiments, the subject is a human or an animal. In some embodiments, the methods further comprise administering an additional cancer therapy. In some embodiments, the additional cancer therapy is selected from among chemotherapy, radiation therapy, immunotherapy, monoclonal antibodies, anti-cancer nucleic acids or proteins, anti-cancer viruses or microorganisms, and any combinations thereof. In some embodiments, the one or more modified immune cells comprises a detectable moiety.

Also described herein, in certain embodiments are methods for preparing modified immune cells for melanoma therapy, comprising contacting one or more immune cells in vitro with a MYC fusion polypeptide, wherein the immune cells are from a donor that has been exposed to one or more tumor antigens and wherein the MYC fusion peptide comprises (i) a protein transduction domain; (ii) a MYC polypeptide sequence and are reactive to a tumor-specific antigen. In some embodiments, the one or more modified immune cells are derived from primary immune cells isolated from a subject having melanoma. In some embodiments, the methods further comprise expanding the primary immune cells in vitro prior to contacting with the MYC fusion peptide. In some embodiments, the methods further comprise expanding the primary immune cells following contacting with the MYC fusion peptide. In some embodiments, the cells are expanded using an anti-CD3 antibody. In some embodiments, the cells are expanded using an irradiated allogenic feeder cells. In some embodiments, the cells are expanded in the presence of an exogenous cytokine. In some embodiments, the cytokine is interleukin-2. In some embodiments, the MYC fusion peptide translocates to the nucleus of the immune cell. In some embodiments, the MYC fusion peptide exhibits a biological activity of MYC. In some embodiments, the MYC fusion peptide further comprises one or more molecules that link the protein transduction domain and the MYC polypeptide. In some embodiments, the MYC fusion peptide comprises a MYC fusion peptide with the following general structure:

protein transduction domain-X-MYC sequence, wherein -X- is molecule that links the protein transduction domain and the MYC sequence. In some embodiments, the protein transduction domain sequence is a TAT protein transduction domain sequence. In some embodiments, the TAT protein transduction domain sequence is selected from the group consisting of TAT[48-57] and TAT[57-48]. In some embodiments, the MYC fusion peptide comprises SEQ ID NO: 1. In some embodiments, the MYC fusion peptide is acetylated. In some embodiments, the one or more modified immune cells have antitumor activity. In some embodiments, the one or more modified immune cells have antitumor activity against melanoma cells in the subject. In some embodiments, the one or more modified immune cells comprise one or more anergic immune cells. In some embodiments, the one or more immune cells comprises one or more lymphocytes. In some embodiments, the one or more lymphocytes comprises a T cell, a B cell, an NK, or any combination thereof. In some embodiments, the T cell is selected from the group consisting of naïve T cells, CD4+ T cells, CD8+ T cells, memory T cells, activated T cells, anergic T cells, tolerant T cells, chimeric T cells, and antigen-specific T cells. In some embodiments, the B cells are selected from the group consisting of naïve B cells, plasma B cells, activated B cells, memory B cells, anergic B cells, tolerant B cells, chimeric B cells, and antigen-specific B cells. In some embodiments, the one or more lymphocytes is a tumor-infiltrating lymphocyte, T-cell receptor modified lymphocyte, or a chimeric antigen receptor modified lymphocyte. In some embodiments, the lymphocyte has a CD8+CD28−CD152− signature. In some embodiments, the lymphocyte has a CD8+CD25+ signature. In some embodiments, the lymphocyte has a CD4+CD25+ signature.

Also described herein, in certain embodiments, are compositions comprising: (a) one or more isolated primary immune cells that have been exposed to a melanoma cell line; and (b) a MYC fusion peptide, comprising (i) a protein transduction domain; (ii) a MYC polypeptide sequence; wherein the one or more primary immune cells are reactive against a melanoma-specific antigen.

Also described herein, in certain embodiments, are any of the aforementioned compositions for use in treating a melanoma. Also described herein, in certain embodiments, are any of the aforementioned compositions for use in the manufacture of a medicament for use in treating a melanoma.

Also described herein, in certain embodiments, are methods for increasing the efficacy of adoptive cell therapy or T-cell therapy in a subject comprising administering any of the aforementioned compositions.

Also described herein, in certain embodiments, are tumor-infiltrating lymphocytes comprising a MYC fusion peptide, comprising (i) a protein transduction domain; (ii) a MYC polypeptide sequence. In some embodiments, the tumor-infiltrating lymphocytes are derived from primary tumor-infiltrating lymphocytes isolated from a subject that has cancer (e.g., melanoma).

Also described herein, in certain embodiments, are lymphocytes comprising a chimeric antigen receptor and a MYC fusion peptide, comprising (i) a protein transduction domain; (ii) a MYC polypeptide sequence. In some embodiments, the lymphocytes are derived from primary lymphocytes isolated from a subject that has cancer (e.g., melanoma).

Also described herein, in certain embodiments, are methods for preparing a composition for adoptive cell therapy comprising contacting one or more primary immune cells with MYC fusion peptide, comprising (i) a protein transduction domain; (ii) a MYC polypeptide sequence, wherein one or more primary immune cells are isolated from a patient having melanoma, and wherein one or more primary immune cells are reactive to a melanoma-specific antigen.

Also provided are kits comprising the MYC-fusion polypeptides and/or MYC-fusion polypeptide-modified immune cells provided herein for use in treating a melanoma. In some embodiments, the kit comprises one for more reagents for the detection of the administered MYC-fusion polypeptides and/or MYC-fusion polypeptide-modified immune cells. In some embodiments, the kit comprises cells for treatment with a MYC-fusion polypeptide provided herein, for example, hematopoietic stem cells, donor leukocytes, T cells, or NK cells. In some embodiments, the kit comprises associated instructions for using the MYC-fusion polypeptides and/or MYC-fusion polypeptide-modified immune cells.

DETAILED DESCRIPTION OF THE INVENTION

Figure 1:
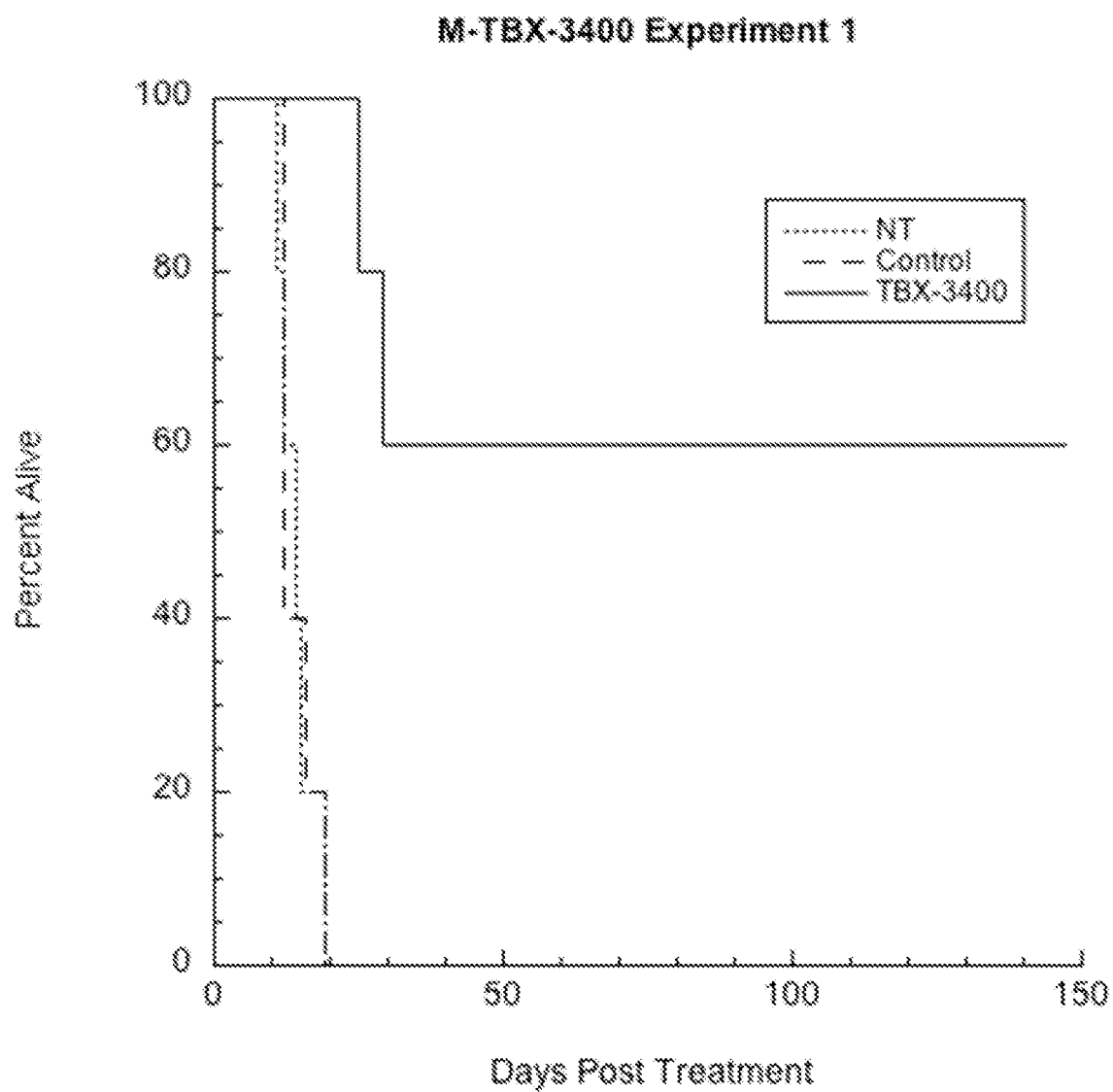
FIG. 1 illustrates results for survival of melanoma tumor-bearing mice following infusion of lymphocytes from tumor-bearing donor mice treated with TAT-MYC for 1 hour. Mice were treated with TAT-MYC lymphocytes, lymph cells treated with a control protein or left untreated. Day of death recorded with day of treatment as Day 0.

The present disclosure is not to be limited in terms of the particular embodiments described in this application, which are intended as single illustrations of individual aspects of the disclosure. All the various embodiments of the present disclosure will not be described herein. Many modifications and variations of the disclosure can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled.

It is to be understood that the present disclosure is not limited to particular uses, methods, reagents, compounds, compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Unless defined otherwise, all technical and scientific terms used herein have the same meaning as commonly understood by one of ordinary skill in the art to which this disclosure belongs.

I. Definitions

The terminology used herein is for the purpose of describing particular embodiments only and is not intended to be limiting of the disclosure. As used herein, the singular forms "a", "an" and "the" are intended to include the plural forms as well, unless the context clearly indicates otherwise.

As used herein, the term "about" means that a value can vary +/−20%, +/−15%, +/−10% or +/−5% and remain within the scope of the present disclosure. For example, "a concentration of about 200 IU/mL" encompasses a concentration between 160 IU/mL and 240 IU/mL.

As used herein, the term "administration" of an agent to a subject includes any route of introducing or delivering the agent to a subject to perform its intended function. Administration can be carried out by any suitable route, including intravenously, intramuscularly, intraperitoneally, or subcutaneously. Administration includes self-administration and the administration by another.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to agents that have the same basic chemical structure as a naturally occurring amino acid, i.e., an α carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. In some embodiments, amino acids forming a polypeptide are in the D form. In some embodiments, the amino acids forming a polypeptide are in the L form. In some embodiments, a first plurality of amino acids forming a polypeptide are in the D form and a second plurality are in the L form.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter code.

The terms "polypeptide," "peptide," and "protein" are used interchangeably herein to refer to a polymer of amino acid residues. The terms apply to naturally occurring amino acid polymers as well as amino acid polymers in which one or more amino acid residues is a non-naturally occurring amino acid, e.g., an amino acid analog. The terms encompass amino acid chains of any length, including full length proteins, wherein the amino acid residues are linked by covalent peptide bonds.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a composition known to exhibit the desired therapeutic effect) and a negative control (a subject or a sample that does not receive the therapy or receives a placebo) are typically employed.

As used herein, the term "effective amount" or "therapeutically effective amount" refers to a quantity of an agent sufficient to achieve a desired therapeutic effect. In the context of therapeutic applications, the amount of a therapeutic peptide administered to the subject can depend on the type and severity of the infection and on the characteristics of the individual, such as general health, age, sex, body weight and tolerance to drugs. It can also depend on the degree, severity and type of disease. The skilled artisan will be able to determine appropriate dosages depending on these and other factors.

As used herein, the term "expression" refers to the process by which polynucleotides are transcribed into mRNA and/or the process by which the transcribed mRNA is subsequently being translated into peptides, polypeptides, or proteins. If the polynucleotide is derived from genomic DNA, expression can include splicing of the mRNA in a eukaryotic cell. The expression level of a gene can be determined by measuring the amount of mRNA or protein in a cell or tissue sample. In one aspect, the expression level of a gene from one sample can be directly compared to the expression level of that gene from a control or reference sample. In another aspect, the expression level of a gene from one sample can be directly compared to the expression level of that gene from the same sample following administration of the compositions disclosed herein. The term "expression" also refers to one or more of the following events: (1) production of an RNA template from a DNA sequence (e.g., by transcription) within a cell; (2) processing of an RNA transcript (e.g., by splicing, editing, 5' cap formation, and/or 3' end formation) within a cell; (3) translation of an RNA sequence into a polypeptide or protein within a cell; (4) post-translational modification of a polypeptide or protein within a cell; (5) presentation of a polypeptide or protein on the cell surface; and (6) secretion or presentation or release of a polypeptide or protein from a cell.

The term "linker" refers to synthetic sequences (e.g., amino acid sequences) that connect or link two sequences, e.g., that link two polypeptide domains. In some embodiments, the linker contains 1, 2, 3, 4, 5, 6, 7, 8, 9, or 10 of amino acid sequences.

The terms "lyophilized," "lyophilization" and the like as used herein refer to a process by which the material (e.g., nanoparticles) to be dried is first frozen and then the ice or frozen solvent is removed by sublimation in a vacuum environment. An excipient can be included in pre-lyophilized formulations to enhance stability of the lyophilized product upon storage. The lyophilized sample can further contain additional excipients.

As used herein the term immune cell refers to any cell that plays a role in the immune response. Immune cells are of hematopoietic origin, and include lymphocytes, such as B cells and T cells; natural killer cells; myeloid cells, such as monocytes, macrophages, dendritic cells, eosinophils, neutrophils, mast cells, basophils, and granulocytes.

The term "lymphocyte" refers to all immature, mature, undifferentiated and differentiated white lymphocyte populations including tissue specific and specialized varieties. It encompasses, by way of non-limiting example, B cells, T cells, NKT cells, and NK cells. In some embodiments, lymphocytes include all B cell lineages including pre-B cells, progenitor B cells, early pro-B cells, late pro-B cells, large pre-B cells, small pre-B cells, immature B cells, mature B cells, plasma B cells, memory B cells, B-1 cells, B-2 cells and anergic AN1/T3 cell populations.

As used herein, the term T-cell includes naïve T cells, CD4+ T cells, CD8+ T cells, memory T cells, activated T cells, anergic T cells, tolerant T cells, chimeric T cells, and antigen-specific T cells.

The term "B cell" or "B cells" refers to, by way of non-limiting example, a pre-B cell, progenitor B cell, early pro-B cell, late pro-B cell, large pre-B cell, small pre-B cell, immature B cell, mature B cell, naïve B cells, plasma B cells, activated B cells, anergic B cells, tolerant B cells, chimeric B cells, antigen-specific B cells, memory B cell, B-1 cell, B-2 cells and anergic AN1/T3 cell populations. In some embodiments, the term B cell includes a B cell that expresses an immunoglobulin heavy chain and/or light chain on its cells surface. In some embodiments, the term B cell includes a B cell that expresses and secretes an immunoglobulin heavy chain and/or light chain. In some embodiments, the term B cell includes a cell that binds an antigen on its cell-surface. In some embodiments disclosed herein, B cells or AN1/T3 cells are utilized in the processes described. In certain embodiments, such cells are optionally substituted with any animal cell suitable for expressing, capable of expressing (e.g., inducible expression), or capable of being differentiated into a cell suitable for expressing an antibody including, e.g., a hematopoietic stem cell, a naïve B cell, a B cell, a pre-B cell, a progenitor B cell, an early Pro-B cell, a late pro-B cell, a large pre-B cell, a small pre-B cell, an immature B cell, a mature B cell, a plasma B cell, a memory B cell, a B-1 cell, a B-2 cell, an anergic B cell, or an anergic AN1/T3 cell.

As used herein "adoptive cell therapeutic composition" refers to any composition comprising cells suitable for adoptive cell transfer. In exemplary embodiments, the adoptive cell therapeutic composition comprises a cell type selected from a group consisting of a tumor infiltrating lymphocyte (TIL), TCR (i.e. heterologous T-cell receptor) modified lymphocytes and CAR (i.e. chimeric antigen receptor) modified lymphocytes. In another embodiment, the adoptive cell therapeutic composition comprises a cell type selected from a group consisting of T-cells, CD8+ cells, CD4+ cells, NK-cells, delta-gamma T-cells, regulatory T-cells and peripheral blood mononuclear cells. In another embodiment, TILs, T-cells, CD8+ cells, CD4+ cells, NK-cells, delta-gamma T-cells, regulatory T-cells or peripheral blood mononuclear cells form the adoptive cell therapeutic composition. In one embodiment, the adoptive cell therapeutic composition comprises T cells.

As used herein "tumor-infiltrating lymphocytes" or TILs refer to white blood cells that have left the bloodstream and migrated into a tumor.

The terms "MYC" and "MYC gene" are synonyms. They refer to a nucleic acid sequence that encodes a MYC polypeptide. A MYC gene comprises a nucleotide sequence of at least 120 nucleotides that is at least 60% to 100% identical or homologous, e.g., at least 60, 65%, 70%, 75%, 80%, 85%, 86%, 87%, 88%, 90%, 91%, 92%, 94%, 95%, 96%, 97%, 98%, or any other percent from about 70% to about 100% identical to sequences of NCBI Accession Number NM-002467. In some embodiments, the MYC gene is a proto-oncogene. In certain instances, a MYC gene is found on chromosome 8, at 8q24.21. In certain instances, a MYC gene begins at 128,816,862 bp from pter and ends at 128,822,856 bp from pter. In certain instances, a MYC gene is about 6 kb. In certain instances, a MYC gene encodes at least eight separate mRNA sequences-5 alternatively spliced variants and 3 unspliced variants.

The terms "MYC protein," "MYC polypeptide," and "MYC sequence" are synonyms and refer to the polymer of amino acid residues disclosed in NCBI Accession Number UniProtKB/Swiss-Prot:P01106.1 (MYC isoform 1) or NP_002458.2 (UniProtKB/Swiss-Prot:P01106.2; MYC isoform 2), and functional homologs, analogs or fragments thereof. The sequence of or UniProtKB/Swiss-Prot: P01106.1 is:

```
                                            (SEQ ID NO: 2)
MPLNVSFTNRNYDLDYDSVQPYFYCDEEENFYQQQQQSELQPPAPSEDIW

KKFELLPTPPLSPSRRSGLCSPSYVAVTPFSLRGDNDGGGGSFSTADQLE

MVTELLGGDMVNQSFICDPDDETFIKNIIIQDCMWSGFSAAAKLVSEKLA

SYQAARKDSGSPNPARGHSVCSTSSLYLQDLSAAASECIDPSVVFPYPLN

DSSSPKSCASQDSSAFSPSSDSLLSSTESSPQGSPEPLVLHEETPPTTSS

DSEEEQEDEEEIDVVSVEKRQAPGKRSESGSPSAGGHSKPPHSPLVLKRC

HVSTHQHNYAAPPSTRKDYPAAKRVKLDSVRVLRQISNNRKCTSPRSSDT

EENVKRRTHNVLERQRRNELKRSFFALRDQIPELENNEKAPKVVILKKAT

AYILSVQAEEQKLISEEDLLRKRREQLKHKLEQLRNSCA
```

The sequence of NP_002458.2 (UniProtKB/Swiss-Prot: P01106.2) is:

```
                                           (SEQ ID NO: 11)
MDFFRVVENQQPPATMPLNVSFTNRNYDLDYDSVQPYFYCDEEENFYQQQ

QQSELQPPAPSEDIWKKFELLPTPPLSPSRRSGLCSPSYVAVTPFSLRGD

NDGGGGSFSTADQLEMVTELLGGDMVNQSFICDPDDETFIKNIIIQDCMW

SGFSAAAKLVSEKLASYQAARKDSGSPNPARGHSVCSTSSLYLQDLSAAA

SECIDPSVVFPYPLNDSSSPKSCASQDSSAFSPSSDSLLSSTESSPQGSP

EPLVLHEETPPTTSSDSEEEQEDEEEIDVVSVEKRQAPGKRSESGSPSAG

GHSKPPHSPLVLKRCHVSTHQHNYAAPPSTRKDYPAAKRVKLDSVRVLRQ

ISNNRKCTSPRSSDTEENVKRRTHNVLERQRRNELKRSFFALRDQIPELE

NNEKAPKVVILKKATAYILSVQAEEQKLISEEDLLRKRREQLKHKLEQLR

NSCA
```

In some embodiments, the MYC polypeptide is a complete MYC polypeptide sequence. In some embodiments, the MYC polypeptide is a partial MYC polypeptide sequence. In some embodiments, the MYC polypeptide comprises at least 400 consecutive amino acids of SEQ ID NO: 2 OR 11. In some embodiments, the MYC polypeptide comprises at least 400 consecutive amino acids of SEQ ID NO: 2 OR 11 and retains at least one MYC activity. In some embodiments, the MYC polypeptide comprises at least 400, at least 410, at least 420, at least 430, or at least 450 consecutive amino acids of SEQ ID NO: 2 OR 11. In some embodiments, the MYC polypeptide comprises at least 400, at least 410, at least 420, at least 430, or at least 450 consecutive amino acids of SEQ ID NO: 2 OR 11 and retains at least one MYC activity. In some embodiments, the MYC polypeptide is c-MYC. In some embodiments, the MYC polypeptide sequence comprises the sequence shown below:

(SEQ ID NO: 3)
MDFFRVVENQQPPATMPLNVSFTNRNYDLDYDSVQPYFYCDEEENFYQQQ

QQSELQPPAPSEDIWKKFELLPTPPLSPSRRSGLCSPSYVAVTPFSLRGD

NDGGGGSFSTADQLEMVTELLGGDMVNQSFICDPDDETFIKNIIQDCMW

SGESAAAKLVSEKLASYQAARKDSGSPNPARGHSVCSTSSLYLQDLSAAA

SECIDPSVVFPYPLNDSSSPKSCASQDSSAFSPSSDSLLSSTESSPQGSP

EPLVLHEETPPTTSSDSEEEQEDEEEIDVVSVEKRQAPGKRSESGSPSAG

GHSKPPHSPLVLKRCHVSTHQHNYAAPPSTRKDYPAAKRVKLDSVRVLRQ

ISNNRKCTSPRSSDTEENVKRRTHNVLERQRRNELKRSFFALRDQIPELE

NNEKAPKVVILKKATAYILSVQAEEQKLISEEDLLRKRREQLKHKLEQL

R.

In some embodiments, the MYC polypeptide sequence comprises the sequence shown below:

(SEQ ID NO: 4)
PLNVSFTNRNYDLDYDSVQPYFYCDEEENFYQQQQQSELQPPAPSEDIWK

KFELLPTPPLSPSRRSGLCSPSYVAVTPFSLRGDNDGGGGSFSTADQLEM

VTELLGGDMVNQSFICDPDDETFIKNIIQDCMWSGFSAAAKLVSEKLAS

YQAARKDSGSPNPARGHSVCSTSSLYLQDLSAAASECIDPSVVFPYPLND

SSSPKSCASQDSSAFSPSSDSLLSSTESSPQGSPEPLVLHEETPPTTSSD

SEEEQEDEEEIDVVSVEKRQAPGKRSESGSPSAGGHSKPPHSPLVLKRCH

VSTHQHNYAAPPSTRKDYPAAKRVKLDSVRVLRQISNNRKCTSPRSSDTE

ENVKRRTHNVLERQRRNELKRSFFALRDQIPELENNEKAPKVVILKKATA

YILSVQAEEQKLISEEDLLRKRREQLKHKLEQLR.

In some embodiments, a MYC polypeptide comprises an amino acid sequence that is at least 40% to 100% identical, e.g., at least 40%, 45%, 50%, 55%, 60%, 65%, 70%, 75%, 80%, 81%, 82%, 83%, 84%, 85%, 86%, 87%, 88%, 90%, 91%, 92%, 94%, 95%, 96%, 97%, 98%, 99%, or any other percent from about 40% to about 100% identical to the sequence of NCBI Accession Number NP002458.2 or UniProtKB/Swiss-Prot Accession Number P01106.1. In some embodiments, MYC polypeptide refers to a polymer of 439 amino acids, a MYC polypeptide that has not undergone any post-translational modifications. In some embodiments, MYC polypeptide refers to a polymer of 439 amino acids that has undergone post-translational modifications. In some embodiments, the MYC polypeptide is 48,804 kDa. In some embodiments, the MYC polypeptide contains a basic Helix-Loop-Helix Leucine Zipper (bHLH/LZ) domain. In some embodiments, the bHLH/LZ domain comprises the sequence of: ELKRSFFALRDQIPELENNEKAPKVVILK-KATAYILSVQAEEQKLISEEDLLRKRREQLKH KLEQLR (SEQ ID NO: 5). In some embodiments, the MYC polypeptide is a transcription factor (e.g., Transcription Factor 64). In some embodiments, the MYC polypeptide contains an E-box DNA binding domain. In some embodiments, the MYC polypeptide binds to a sequence comprising CACGTG. In some embodiments, the MYC polypeptide promotes one or more of cell survival and/or proliferation. In some embodiments, a MYC polypeptide includes one or more of those described above, and includes one or more post-translational modifications (e.g., acetylation). In some embodiments, the MYC polypeptides comprise one or more additional amino acid residues at the N-terminus or C-terminus of the polypeptide. In some embodiments, the MYC polypeptides are fusion proteins. In some embodiments, the MYC polypeptides are linked to one or more additional peptides at the N-terminus or C-terminus of the polypeptide.

Proteins suitable for use in the methods described herein also includes functional variants, including proteins having between 1 to 15 amino acid changes, e.g., 1, 2, 3, 4, 5, 6, 7, 8, 9, 10, 11, 12, 13, 14, or 15 amino acid substitutions, deletions, or additions, compared to the amino acid sequence of any protein described herein. In other embodiments, the altered amino acid sequence is at least 75% identical, e.g., 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the amino acid sequence of any protein inhibitor described herein. Such sequence-variant proteins are suitable for the methods described herein as long as the altered amino acid sequence retains sufficient biological activity to be functional in the compositions and methods described herein. Where amino acid substitutions are made, the substitutions can be conservative amino acid substitutions. Among the common, naturally occurring amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff et al., (1992), *Proc. Natl Acad. Sci. USA,* 89:10915-10919). Accordingly, the BLOSUM62 substitution frequencies are used to define conservative amino acid substitutions that, in some embodiments, are introduced into the amino acid sequences described or disclosed herein. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

The phrases "E-box sequence" and "enhancer box sequence" are used interchangeably herein and mean the nucleotide sequence CANNTG, wherein N is any nucleotide. In certain instances, the E-box sequence comprises CACGTG. In certain instances, the basic helix-loop-helix domain of a transcription factor encoded by MYC binds to the E-box sequence. In certain instances the E-box sequence is located upstream of a gene (e.g., p21, Bcl-2, or ornithine decarboxylase). In certain instances, the MYC polypeptide contains an E-box DNA binding domain. In certain instances, the E-box DNA binding domain comprises the sequence of KRRTHNVLERQRRN (SEQ ID NO: 6). In certain instances, the binding of the transcription factor encoded by MYC to the E-box sequence, allows RNA polymerase to transcribe the gene downstream of the E-box sequence.

The term "MYC activity" or "MYC biological activity" or "biologically active MYC" includes one or more of enhancing or inducing cell survival, cell proliferation, and/or antibody production. By way of example and not by way of limitation, MYC activity includes enhancement of expansion of anti-CD3 and anti-CD28 activated T-cells and/or increased proliferation of long-term self-renewing hematopoietic stem cells. MYC activity also includes entry into the nucleus of a cell, binding to a nucleic acid sequence (e.g., binding an E-box sequence), and/or inducing expression of MYC target genes.

The terms "patient," "subject," "individual," and the like are used interchangeably herein, and refer to an animal, typically a mammal. In one embodiment, the patient, subject, or individual is a mammal. In one embodiment, the patient, subject or individual is a human. In some embodiments the patient, subject or individual is an animal, such as, but not limited to, domesticated animals, such as equine, bovine, murine, ovine, canine, and feline.

The terms "protein transduction domain (PTD)" or "transporter peptide sequence" (also known as cell permeable proteins (CPP) or membrane translocating sequences (MTS)) are used interchangeably herein to refer to small peptides that are able to ferry much larger molecules into cells independent of classical endocytosis. In some embodiments, a nuclear localization signal can be found within the protein transduction domain, which mediates further translocation of the molecules into the cell nucleus.

The terms "treating" or "treatment" as used herein covers the treatment of a disease in a subject, such as a human, and includes: (i) inhibiting a disease, i.e., arresting its development; (ii) relieving a disease, i.e., causing regression of the disease; (iii) slowing progression of the disease; and/or (iv) inhibiting, relieving, or slowing progression of one or more symptoms of the disease. With respect to a melanoma, "treating" or "treatment" also encompasses regression of a tumor, slowing tumor growth, inhibiting metastasis of a melanoma tumor, inhibiting relapse or recurrent melanoma and/or maintaining remission.

It is also to be appreciated that the various modes of treatment or prevention of medical diseases and conditions as described are intended to mean "substantial," which includes total but also less than total treatment or prevention, and wherein some biologically or medically relevant result is achieved. The treatment can be a continuous prolonged treatment for a chronic disease or a single, or few time administrations for the treatment of an acute condition.

The term "therapeutic" as used herein means a treatment and/or prophylaxis. A therapeutic effect is obtained by suppression, remission, or eradication of a disease state.

II. Overview

The present disclosure relates, in part, to the treatment of melanoma in a subject by administering a composition comprising one or more immune cells having anti-tumor activity (e.g., immune cells that modulate a response against a tumor, such as tumor-infiltrating lymphocytes (TILs)), wherein the one or more immune cells are contacted with a PTD-MYC fusion polypeptide in vitro prior to administration to the subject. In some embodiments, the immune cells are obtained from a donor subject that has a melanoma tumor. In some embodiments, the cells are autologous to the subject receiving treatment. In some embodiments, the melanoma is a superficial spreading melanoma, a nodular melanoma, a lentigo maligna melanoma, or an acral melanoma.

The present disclosure is based, at least in part, on the discovery, that treating lymphocytes isolated from a donor subject having a melanoma tumor with a MYC fusion polypeptide containing a MYC polypeptide and a protein transduction domain (PTD), such as the HIV TAT protein transduction domain, and administering the treated lymphocytes to a subject bearing a melanoma tumor significantly increases the survival of the tumor-bearing subject. The examples provided herein demonstrate that immune cells extracted from the lymph nodes of a melanoma-bearing mouse had significantly increased therapeutic efficacy when the cells were treated with a TAT-MYC fusion protein in vitro prior to administration to a second melanoma-bearing mice. These data support that adoptive cell transfer using anti-tumor immune cells treated with a PTD-MYC fusion polypeptide can be employed in the treatment of tumors, such as melanoma tumors.

In some embodiments, the method for the treatment of melanoma in a subject comprises administering immune cells that have been contacted in vitro with a PTD-MYC fusion polypeptide. In some embodiments, the immune cells for use in the present methods are primed in vivo with melanoma tumor antigen. In some embodiments, the immune cells are from a donor having melanoma. In some embodiments, the immune cells are from a donor having a solid tumor, such as a melanoma tumor. In some embodiments, the immune cells are contacted in vivo with a melanoma tumor antigen. In some embodiments, the immune cells are from a donor that has been exposed to a one or more melanoma tumor antigens. In some embodiments, the immune cells are from a donor that has been exposed to an anti-tumor vaccine. In some embodiments, the immune cells are B cells, T cells, NK cells, or any combination thereof. In some embodiments, the immune cells are tumor infiltrating lymphocytes (TIL). In some embodiments, the immune cells are chimeric antigen receptor (CAR)-T cells.

In some embodiments, the method for the treatment of melanoma in a subject comprises administering one or more modified immune cells to the subject in need thereof, wherein the one or more modified immune cells comprise a MYC fusion peptide comprising (i) a protein transduction domain; (ii) a MYC polypeptide sequence and are reactive to a melanoma tumor-specific antigen.

In some embodiments, the method for the treatment of melanoma in a subject comprises the steps of:

a) contacting immune cells in vitro with a MYC fusion polypeptide, wherein the immune cells are from a donor that has been exposed to one or more melanoma tumor antigens and the MYC fusion peptide comprising (i) a protein transduction domain; (ii) a MYC polypeptide sequence; and b) administering the contacted immune cells to the melanoma tumor-bearing subject, whereby the melanoma is treated.

In some embodiments, contacting the immune cells in vitro with a PTD-MYC fusion polypeptide is performed by culturing the immune cells in the presence of the MYC fusion polypeptide. In some embodiments, the immune cells are cultured in the presence of one or more cytokines and/or growth factors (e.g., interleukin-2 (IL-2), IL-4, IL-7, IL-9, and IL-15). In some embodiments, the immune cells are not expanded prior to administration. In some embodiments, the immune cells are expanded prior to administration. In some embodiments, the donor and subject for treatment are the same.

In some embodiments, the immune cells are tumor-infiltrating lymphocytes. In some embodiments, the tumor-infiltrating lymphocytes are autologous tumor-infiltrating lymphocytes. Accordingly, in some embodiments, the method for the treatment of melanoma in a subject comprises administering lymphocytes that have been contacted in vitro with a PTD-MYC fusion polypeptide, wherein the immune cells are from lymphocytes are autologous tumor-infiltrating lymphocytes from the subject.

In some embodiments, the method for the treatment of melanoma in a subject comprises the steps of:

a) contacting lymphocytes in vitro with a PTD-MYC fusion polypeptide, wherein the lymphocytes are autologous tumor-infiltrating lymphocytes from the subject, and b) administering the contacted autologous tumor-infiltrating lymphocytes to the subject, whereby the melanoma is treated.

Methods of Obtaining and Preparing Immune Cells for Transfer

Immune cells for use in the methods provided herein can be obtained using any suitable method known in the art. In some embodiments, the immune cells are primary immune cells. In some embodiments, the immune cells are lymphocytes, such as T and B cells. In some embodiments, the immune cells are natural killer (NK) cells. In some embodiments, the immune cells are a mixture of lymphocytes and NK cells. In some embodiments, the immune cells are peripheral blood mononuclear cells (PBMC). In some embodiments, the immune cells are T cells that have infiltrated a tumor (e.g., tumor infiltrating lymphocytes). In some embodiments, the T cells are removed during surgery of a melanoma tumor or a metastatic tumor in a subject. For example, in some embodiments, the T cells are isolated after removal of tumor tissue by biopsy. In some embodiments, the immune cells are modified following isolation from a donor. In some embodiments, the immune cells are chimeric antigen receptor (CAR)-T cells.

In some embodiments, the T cells are isolated from sample containing a population of cells, such as a blood, lymph or tissue biopsy sample. T cells can be isolated from a population of cells by any means known in the art. In one embodiment, the method comprises obtaining a bulk population of T cells from a tumor sample by any suitable method known in the art. For example, a bulk population of T cells can be obtained from a tumor sample by dissociating the tumor sample into a cell suspension from which specific cell populations can be selected. Suitable methods of obtaining a bulk population of T cells can include, but are not limited to, any one or more of mechanically dissociating (e.g., mincing) the tumor, enzymatically dissociating (e.g., digesting) the tumor, and aspiration (e.g., as with a needle).

The bulk population of T cells obtained from a tumor sample can comprise any suitable type of T cell. Preferably, the bulk population of T cells obtained from a tumor sample comprises tumor infiltrating lymphocytes (TILs).

The tumor sample can be obtained from any mammal. Unless stated otherwise, as used herein, the term "mammal" refers to any mammal including, but not limited to, mammals of the order Logomorpha, such as rabbits; the order Carnivora, including Felines (cats) and Canines (dogs); the order Artiodactyla, including Bovines (cows) and Swines (pigs); or of the order Perssodactyla, including Equines (horses). The mammals can be non-human primates, e.g., of the order Primates, Ceboids, or Simoids (monkeys) or of the order Anthropoids (humans and apes). In some embodiments, the mammal can be a mammal of the order Rodentia, such as mice and hamsters. Preferably, the mammal is a non-human primate or a human. An exemplary mammal is a human. In some embodiments, the subject to receive the immune cells is also the donor of the tumor sample (i.e., autologous ACT)

T cells can be obtained from a number of sources, including peripheral blood mononuclear cells, bone marrow, lymph node tissue, spleen tissue, and tumors. In certain embodiments, T cells can be obtained from a unit of blood collected from a subject using any number of techniques known to the skilled artisan, such as Ficoll separation. In one embodiment, cells from the circulating blood of an individual are obtained by apheresis or leukopheresis. The apheresis product typically contains lymphocytes, including T cells, monocytes, granulocytes, B cells, other nucleated white blood cells, red blood cells, and platelets. In one embodiment, the cells collected by apheresis can be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and can lack magnesium or can lack many if not all divalent cations. Initial activation steps in the absence of calcium lead to magnified activation. As those of ordinary skill in the art would readily appreciate, a washing step can be accomplished by methods known to those in the art, such as by using a semi-automated "flow-through" centrifuge (for example, the Cobe 2991 cell processor) according to the manufacturer's instructions. After washing, the cells can be resuspended in a variety of biocompatible buffers, such as, for example, Ca-free, Mg-free PBS. Alternatively, the undesirable components of the apheresis sample can be removed and the cells directly resuspended in culture media.

In another embodiment, T cells are isolated from peripheral blood lymphocytes by lysing the red blood cells and depleting the monocytes, for example, by centrifugation through a PERCOLL™ gradient. A specific subpopulation of T cells, such as CD28+, CD4+, CDC, CD45RA+, and CD45RO+ T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, or XCYTE DYNABEADS™ for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another embodiment, the time period is 10 to 24 hours. In one embodiment, the incubation time period is 24 hours. For isolation of T cells from patients with leukemia, use of longer incubation times, such as 24 hours, can increase cell yield. Longer incubation times can be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells.

Enrichment of a T cell population by negative selection can be accomplished with a combination of antibodies directed to surface markers unique to the negatively selected cells. In one embodiment, the method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

Further, monocyte populations (i.e., CD14+ cells) can be depleted from blood preparations by a variety of methodologies, including anti-CD14 coated beads or columns, or utilization of the phagocytotic activity of these cells to facilitate removal. Accordingly, in one embodiment, the invention uses paramagnetic particles of a size sufficient to be engulfed by phagocytotic monocytes. In certain embodiments, the paramagnetic particles are commercially available beads, for example, those produced by Life Technologies under the trade name Dynabeads™. In one embodiment, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be isolated. In certain embodiments the irrelevant beads include beads coated with sheep anti-mouse antibodies, goat anti-mouse antibodies, and human serum albumin.

In brief, such depletion of monocytes is performed by preincubating T cells isolated from whole blood, apheresed peripheral blood, or tumors with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology can be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after depletion.

For isolation of a desired population of cells by positive or negative selection, the concentration of cells and surface (e.g., particles such as beads) can be varied. In certain embodiments, it can be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that can weakly express target antigens of interest, such as CD28-negative T cells, or from samples where there are many tumor cells present (i.e., leukemic blood, tumor tissue, etc). Such populations of cells can have therapeutic value and would be desirable to obtain. For example, using high concentration of cells allows more efficient selection of CD8+ T cells that normally have weaker CD28 expression.

In a related embodiment, it can be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is $5 \times 10^6$/ml. In other embodiments, the concentration used can be from about $1 \times 10^5$/ml to $1 \times 10^6$/ml, and any integer value in between.

T cells can also be frozen. The freeze and subsequent thaw step can provide a more uniform product by removing granulocytes and to some extent monocytes in the cell population. After a washing step to remove plasma and platelets, the cells can be suspended in a freezing solution. While many freezing solutions and parameters are known in the art and will be useful in this context, one method involves using PBS containing 20% DMSO and 8% human serum albumin, or other suitable cell freezing media, the cells then are frozen to −80° C. at a rate of 1° per minute and stored in the vapor phase of a liquid nitrogen storage tank. Other methods of controlled freezing can be used as well as uncontrolled freezing immediately at −20° C. or in liquid nitrogen.

T cells for use in the present invention can also be antigen-specific T cells. For example, tumor-specific T cells can be used. In certain embodiments, antigen-specific T cells can be isolated from a patient of interest, such as a patient afflicted with a melanoma, such as patient with a melanoma tumor. In some embodiments, the patient has melanoma.

In one embodiment neoepitopes are determined for a subject and T cells specific to these antigens are isolated. Antigen-specific cells for use in expansion can also be generated in vitro using any number of methods known in the art, for example, as described in U.S. Patent Publication No. US 20040224402 entitled, Generation And Isolation of Antigen-Specific T Cells, or in U.S. Pat. No. 6,040,177. Antigen-specific cells for use in the present invention can also be generated using any number of methods known in the art, for example, as described in Current Protocols in Immunology, or Current Protocols in Cell Biology, both published by John Wiley & Sons, Inc., Boston, Mass.

In a related embodiment, it can be desirable to sort or otherwise positively select (e.g. via magnetic selection) the antigen specific cells prior to or following one or two rounds of expansion. Sorting or positively selecting antigen-specific cells can be carried out using peptide-MEW tetramers (Altman, et al., *Science*. 1996 Oct. 4; 274(5284):94-6). In another embodiment the adaptable tetramer technology approach is used (Andersen et al., 2012 Nat Protoc. 7:891-902). Tetramers are limited by the need to utilize predicted binding peptides based on prior hypotheses, and the restriction to specific HLAs. Peptide-MHC tetramers can be generated using techniques known in the art and can be made with any MEW molecule of interest and any antigen of interest as described herein. Specific epitopes to be used in this context can be identified using numerous assays known in the art. For example, the ability of a polypeptide to bind to MEW class I can be evaluated indirectly by monitoring the ability to promote incorporation of $^{125}$I labeled β2-microglobulin (β2m) into MEW class I/β2m/peptide heterotrimeric complexes (see Parker et al., J. Immunol. 152:163, 1994).

In some embodiments, the T cells are recombinantly modified to express a modified or chimeric receptor (e.g., chimeric antigen receptor (CAR) modified T cells).

In one embodiment, cells are directly labeled with an epitope-specific reagent for isolation by flow cytometry followed by characterization of phenotype and TCRs. In one embodiment, T cells are isolated by contacting the T cell specific antibodies. Sorting of antigen-specific T cells, or generally any cells of the present invention, can be carried out using any of a variety of commercially available cell sorters, including, but not limited to, MoFlo sorter (Dako-Cytomation, Fort Collins, Colo.), FACSAria™, FACSArray™, FACSVantage™, BD™ LSR II, and FACSCalibur™ (BD Biosciences, San Jose, Calif.).

In one embodiment, the method comprises selecting cells that also express CD3. The method can comprise specifically selecting the cells in any suitable manner. Preferably, the selecting is carried out using flow cytometry. The flow cytometry can be carried out using any suitable method known in the art. The flow cytometry can employ any suitable antibodies and stains. Preferably, the antibody is chosen such that it specifically recognizes and binds to the particular biomarker being selected. For example, the specific selection of CD3, CD8, TIM-3, LAG-3, 4-1BB, or PD-1 can be carried out using anti-CD3, anti-CD8, anti-TIM-3, anti-LAG-3, anti-4-1BB, or anti-PD-1 antibodies, respectively. The antibody or antibodies can be conjugated to a bead (e.g., a magnetic bead) or to a fluorochrome. Preferably, the flow cytometry is fluorescence-activated cell sorting (FACS). TCRs expressed on T cells can be selected based on reactivity to autologous tumors. Additionally, T cells that are reactive to tumors can be selected for based on markers using the methods described in patent publication Nos. WO2014133567 and WO2014133568, herein incorporated by reference in their entirety. Additionally, activated T cells can be selected for based on surface expression of CD107a.

In one embodiment, the method further comprises expanding the numbers of T cells in the enriched cell population. Such methods are described in U.S. Pat. No. 8,637,307 and is herein incorporated by reference in its entirety. The T cells can be expanded before or after treatment of the cells with the PTD-MYC polypeptide. The numbers of T cells can be increased at least about 3-fold (or 4-, 5-, 6-, 7-, 8-, or 9-fold), more preferably at least about 10-fold (or 20-, 30-, 40-, 50-, 60-, 70-, 80-, or 90-fold), more preferably at least about 100-fold, more preferably at least about 1,000 fold, or most preferably at least about 100,000-fold. The numbers of T cells can be expanded using any suitable method known in the art. Exemplary methods of expanding the numbers of cells are described in patent publication No. WO 2003057171, U.S. Pat. No. 8,034,334, and U.S. Patent Application Publication No. 2012/0244133, each of which is incorporated herein by reference.

In one embodiment, ex vivo T cell expansion can be performed by isolation of T cells and subsequent stimulation or activation followed by further expansion. In one embodiment of the invention, the T cells can be stimulated or activated by a single agent. In another embodiment, T cells are stimulated or activated with two agents, one that induces a primary signal and a second that is a co-stimulatory signal. Ligands useful for stimulating a single signal or stimulating a primary signal and an accessory molecule that stimulates a second signal can be used in soluble form. Ligands can be attached to the surface of a cell, to an Engineered Multivalent Signaling Platform (EMSP), or immobilized on a surface. In a one embodiment both primary and secondary agents are co-immobilized on a surface, for example a bead or a cell. In one embodiment, the molecule providing the primary activation signal can be a CD3 ligand, and the co-stimulatory molecule can be a CD28 ligand or 4-1BB ligand. In some embodiments, the cells are expanded by stimulation with one or more antigens, such as a melanoma tumor antigen or antigens derived from the patient's tumor.

In some embodiments, the isolated immune cells are immediately treated with the PTD-MYC fusion polypeptide following isolation. In other embodiments, the isolated immune cells are stored in a suitable buffer and frozen prior to treatment with the PTD-MYC fusion polypeptide. In some embodiments, the isolated immune cells are immediately treated with the PTD-MYC fusion polypeptide following isolation and the treated cells are stored in a suitable buffer and frozen until needed for administration to the patient.

In certain embodiments, the isolated immune cells (e.g., a mixed population immune cells or isolated types, such as tumor infiltrating lymphocytes) are contacted with a composition containing a PTD-MYC fusion polypeptide for a period of time sufficient to be taken up by the cells. In some embodiments, the immune cells are contacted with a composition containing a PTD-MYC fusion polypeptide for less than about 24 hours, less than about 23 hours, less than about 22 hours, less than about 21 hours, less than about 20 hours, less than about 19 hours, less than about 18 hours, less than about 17 hours, less than about 16 hours, less than about 15 hours, less than about 14 hours, less than about 13 hours, less than about 12 hours, less than about 11 hours, less than about 10 hours, less than about 9 hours, less than about 8 hours, less than about 7 hours, less than about 6 hours, less than about 5 hours, less than about 4 hours, less than about 3 hours, less than about 2 hours, or less than about 1 hour.

In certain embodiments, the immune cells are contacted with a composition containing a PTD-MYC fusion polypeptide for less than about 55 minutes, less than about 50 minutes, less than about 45 minutes, less than about 40 minutes, less than about 35 minutes, less than about 30 minutes, less than about 29 minutes, less than about 28 minutes, less than about 27 minutes, less than about 26 minutes, less than about 25 minutes, less than about 24 minutes, less than about 23 minutes, less than about 22 minutes, less than about 21 minutes, less than about 20 minutes, less than about 19 minutes, less than about 18 minutes, less than about 17 minutes, less than about 16 minutes, less than about 15 minutes, less than about 14 minutes, less than about 13 minutes, less than about 12 minutes, less than about 11 minutes, or less than about 10 minutes. In certain embodiments, the immune cells are contacted with a composition containing a PTD-MYC fusion polypeptide for about 1 hour.

In certain embodiments, the immune cells are contacted with a composition containing a PTD-MYC fusion polypeptide for 24 hours or longer. In certain embodiments, the immune cells are contacted with a composition containing a PTD-MYC fusion polypeptide for less than about 12 days, less than about 11 days, less than about 10 days, less than about 9 days, less than about 8 days, less than about 7 days, less than about 6 days, less than about 5 days, less than about 4 days, less than about 2 days, or less than about 1 day.

In certain embodiments that may be combined with any of the preceding embodiments, the cells are contacted with a MYC-fusion polypeptide at a concentration of 0.5 µg/ml to 500 µg/ml. 0.5 µg/ml, at least 0.6 µg/ml, at least 0.7 µg/ml, at least 0.8 µg/ml, at least 0.9 µg/ml, at least 1 µg/ml, at least 2 µg/ml, at least 3 µg/ml, at least 4 µg/ml, at least 5 µg/ml, at least 6 µg/ml, at least 7 µg/ml, at least 8 µg/ml, at least 9 µg/ml, at least 10 µg/ml, at least 15 µg/ml, at least 20 µg/ml, at least 25 µg/ml, at least 30 µg/ml, at least 35 µg/ml, at least 40 µg/ml, at least 45 µg/ml, at least 50 µg/ml, at least 55 µg/ml, at least 60 µg/ml, at least 65 µg/ml, at least 70 µg/ml, at least 75 µg/ml, at least 80 µg/ml, at least 85 µg/ml, at least 90 µg/ml, at least 95 µg/ml, or at least 100 µg/ml.

MYC Fusion Proteins

In some embodiments, the PTD-MYC fusion polypeptide comprises a protein transduction domain (PTD), a MYC polypeptide that promotes one or more of cell survival or proliferation, and optionally a protein tag domain, e.g., one or more amino acid sequences that facilitate purification of the fusion protein. In some embodiments, a cell contacted with MYC polypeptide exhibits increased survival time (e.g., as compared to an identical or similar cell of the same type that was not contacted with MYC), and/or increased proliferation (e.g., as compared to an identical or similar cell of the same type that was not contacted with MYC).

In some embodiments, the fusion protein comprises (a) a protein transduction domain; and (b) a MYC polypeptide sequence. In some embodiments, the fusion peptide is a peptide of Formula (I):

protein transduction domain-MYC polypeptide sequence.

In some embodiments, a fusion peptide disclosed herein comprises (a) a protein transduction domain; (b) a MYC polypeptide sequence; and (c) one or more molecules that link the protein transduction domain and the MYC polypeptide sequence. In some embodiments, the fusion peptide is a peptide of Formula (II):

protein transduction domain-X-MYC polypeptide sequence, wherein -X- is molecule that links the protein transduction domain and the MYC polypeptide sequence. In some embodiments, -X- is at least one amino acid.

In some embodiments, a fusion peptide disclosed herein comprises (a) a protein transduction domain; (b) a MYC polypeptide sequence; (c) at least two protein tags; and (d) optionally linker(s). In some embodiments, the fusion peptide is a peptide of Formula (III-VI):

protein transduction domain-X-MYC polypeptide sequence-X-protein tag 1-X-protein tag 2 (Formula (III)), or protein transduction domain-MYC polypeptide sequence-X-protein tag 1-X-protein tag 2 (Formula (IV)), or protein transduction domain-MYC polypeptide sequence-protein tag 1-X-protein tag 2 (Formula (V)), or protein transduction domain-MYC polypeptide sequence-protein tag 1-protein tag 2 (Formula (VI)), wherein -X- is a linker. In some embodiments, -X- is one or more amino acids.

In some embodiments, a fusion peptide disclosed herein comprises (a) a protein transduction domain; (b) a MYC polypeptide sequence; (c) a 6-histidine tag; (d) a V5 epitope tag; and (e) optionally linker(s). In some embodiments, the fusion peptide is a peptide of Formula (VII-XIV):

protein transduction domain-X-MYC polypeptide sequence-X-6-histidine tag-X-V5 epitope tag (Formula (VII)), or protein transduction domain-MYC polypeptide sequence-X-6-histidine tag-X-V5 epitope tag (Formula (VIII)), or protein transduction domain-MYC polypeptide sequence-6-histidine tag-X-V5 epitope tag (Formula (IX)), or protein transduction domain-MYC polypeptide sequence-6-histidine tag-V5 epitope tag (Formula (X)), protein transduction domain-X-MYC polypeptide sequence-X-V5 epitope tag-X-6-histidine tag (Formula (XI)), or protein transduction domain-MYC polypeptide sequence-X-V5 epitope tag-X-6-histidine tag (Formula (XII)), or protein transduction domain-MYC polypeptide sequence-V5 epitope tag-X-6-histidine tag (Formula (XIII)), or protein transduction domain-MYC polypeptide sequence-V5 epitope tag-6-histidine tag (Formula (XIV)), wherein -X- is a linker. In some embodiments, -X- is one or more amino acids.

As noted above, in some embodiments, the MYC fusion protein comprises one or more linker sequences. The linker sequences can be employed to link the protein transduction domain, MYC polypeptide sequence, V5 epitope tag and/or 6-histidine tag of the fusion protein. In some embodiments, the linker comprises one or more amino acids. In some embodiments, the amino acid sequence of the linker comprises KGELNSKLE. In some embodiments, the linker comprises the amino acid sequence of RTG.

Protein Transduction Domain (PTD)

In some embodiments, the MYC fusion protein includes a protein transduction domain. Peptide transport provides an alternative for delivery of small molecules, proteins, or nucleic acids across the cell membrane to an intracellular compartment of a cell. One non-limiting example and well-characterized protein transduction domain (PTD) is a TAT-derived peptide. Frankel et al., (see, e.g., U.S. Pat. Nos. 5,804,604, 5,747,641, 5,674,980, 5,670,617, and 5,652,122) demonstrated transport of a cargo protein (β-galactosidase or horseradish peroxidase) into a cell by conjugating a peptide containing amino acids 48-57 of TAT to the cargo protein. In some embodiments, TAT comprises an amino acid sequence of MRKKRRQRRR (SEQ ID NO: 7).

Another non-limiting example of a PTD is penetratin. Penetratin can transport hydrophilic macromolecules across the cell membrane (Derossi et al., *Trends Cell Biol.*, 8:84-87 (1998) incorporated herein by reference in its entirety). Penetratin is a 16 amino acid peptide that corresponds to amino acids 43-58 of the homeodomain of Antennapedia, a *Drosophila* transcription factor which is internalized by cells in culture.

Yet another non-limiting example of a PTD is VP22. VP22, a tegument protein from Herpes simplex virus type 1 (HSV-1), has the ability to transport proteins and nucleic acids across a cell membrane (Elliot et al., *Cell* 88:223-233, 1997, incorporated herein by reference in its entirety). Residues 267-300 of VP22 are necessary but cannot be sufficient for transport. Because the region responsible for transport function has not been identified, the entire VP22 protein is commonly used to transport cargo proteins and nucleic acids across the cell membrane (Schwarze et al., *Trends Pharmacol Sci*, 21:45-48, 2000).

In some embodiments, the PTD-MYC fusion polypeptide includes a protein transduction domain. By way of example, but not by way of limitation, in some embodiments, the protein transduction domain comprises the protein transduction domain of one or more of TAT, penetratin, VP22, vpr, EPTD, R9, R15, VP16, and Antennapedia. In some embodiments, the protein transduction domain comprises the protein transduction domain of one or more of TAT, penetratin, VP22, vpr, and EPTD. In some embodiments, the protein transduction domain comprises the protein transduction domain of at least one of TAT, penetratin, VP22, vpr, EPTD, R9, R15, VP16, and Antennapedia. In some embodiments, the protein transduction domain comprises a synthetic protein transduction domain (e.g., polyarginine or PTD-5). In particular embodiments, the protein transduction domain comprises a TAT protein transduction domain. In some embodiments, the protein transduction domain is covalently linked to the MYC polypeptide. In some embodiments, the protein transduction domain is linked to the MYC polypeptide via a peptide bond. In some embodiments, the protein transduction domain is linked to the MYC polypeptide via a linker sequence. In some embodiments, the linker comprises a short amino acid sequence. By way of example, but not by way of limitation, in some embodiments, the linker sequences is 1, 2, 3, 4, 5, 6, 7, 8, 9, or 10 amino acids in length.

The MYC fusion protein of the present technology can be arranged in any desired order. For example, in some embodiments, the MYC fusion protein can be arranged in order of a) the protein transduction domain linked in frame to the MYC polypeptide, b) the MYC polypeptide linked in frame to the V5 domain, and c) the V5 domain linked in frame to the 6-histidine epitope tag. In some embodiments, the MYC fusion protein has an order of components of a) the MYC polypeptide linked in frame to the protein transduction domain, b) the protein transduction domain linked in frame to the V5 domain, and c) the V5 domain linked in frame to the 6-histidine epitope tag. In some embodiments, additional amino acid sequences can be included between each of the sequences. In some embodiments, additional amino acids can be included at the start and/or end of the polypeptide sequences.

In some embodiments, the protein transduction domain is a TAT protein transduction domain. In some embodiments, the protein transduction domain is $TAT_{[48-57]}$. In some embodiments, the protein transduction domain is $TAT_{[57-48]}$.

Protein Tag Domains

In some embodiments, the MYC fusion protein comprises a protein tag domain that comprises one or more amino acid sequences that facilitate purification of the fusion protein. In some embodiments, the protein tag domain comprises one or more of a polyhistidine tag, and an epitope tag. By way of example, but not by way of limitation, exemplary tags include one or more of a V5, a histidine-tag (e.g., a 6-histidine tag), HA (hemagglutinin) tags, FLAG tag, CBP (calmodulin binding peptide), CYD (covalent yet dissociable NorpD peptide), StrepII, or HPC (heavy chain of protein C). In some embodiments, the protein tag domain comprise about 10 to 20 amino acids in length. In some embodiments, the protein tag domain comprises 2 to 40 amino acids in length, for example 6-20 amino acids in length. In some embodiments, two of the above listed tags (for example, V5 and the HIS-tag) are used together to form the protein tag domain.

In some embodiments, the histidine tag is a 6-histidine tag. In some embodiments, the histidine tag comprises the sequence HHHHHH (SEQ ID NO:8). In some embodiments, the fusion peptide disclosed herein comprises a V5 epitope tag. In some embodiments, the V5 tag comprises the amino acid sequence of: GKPIPNPLLGLDST (SEQ ID NO:9). In some embodiments, the V5 tag comprises the amino acid sequence of IPNPLLGLD (SEQ ID NO:10).

The protein tags can be added to the fusion protein disclosed herein by any suitable method. By way of example, but not by way of limitation, in some embodiments, a TAT-MYC polypeptide sequence is cloned into an expression vector encoding one or more protein tags, e.g., a polyHis-tag and/or a V5 tag. In some embodiments, a polyhistidine tag and/or a V5 tag is added by PCR (i.e., the PCR primers comprise a polyhistidine sequence and/or V5 sequence).

Construction of PTD-MYC Fusion Polypeptides

PTD-MYC fusion polypeptides (e.g., TAT-MYC fusion polypeptide) disclosed herein can be constructed by methods well known in the art. By way of example, but not by way of limitation, a nucleotide sequence encoding a TAT-MYC fusion polypeptide can be generated by PCR. In some embodiments, a forward primer for a human MYC sequence comprises an in frame N-terminal 9-amino-acid sequence of the TAT protein transduction domain (e.g., RKKRRQRRR). In some embodiments, a reverse primer for a human MYC sequence is designed to remove the stop codon. In some embodiments, the PCR product is cloned into any suitable expression vector. In some embodiments, the expression vector comprises a polyhistidine tag and a V5 tag.

In some embodiments, a fusion peptide disclosed herein comprises (a) TAT, and (b) c-MYC. In some embodiments, a fusion peptide disclosed herein comprises (a) $TAT_{[48-57]}$, and (b) c-MYC. In some embodiments, a fusion peptide disclosed herein comprises (a) $TAT_{[57-48]}$, and (b) c-MYC.

In some embodiments, a fusion peptide disclosed herein comprises (a) TAT, (b) c-MYC, (c) linker(s), (d) V5 tag, and (e) 6-histidine tag. In some embodiments, a fusion peptide disclosed herein comprises (a) $TAT_{[48-57]}$, (b) c-MYC, (c) linker(s), (d) V5 tag, and (e) 6-histidine tag. In some embodiments, a fusion peptide disclosed herein comprises (a) $TAT_{[57-48]}$, (b) c-MYC, (c) linker(s), (d) V5 tag, and (e) 6-histidine tag.

In some embodiments, the PTD-MYC fusion polypeptide comprises SEQ ID NO: 1; in some embodiments, the PTD-MYC fusion polypeptide is SEQ ID NO: 1.

```
                                            (SEQ ID NO: 1)
MRKKRRQRRRPLNVSFTNRNYDLDYDSVQPYFYCDEEENFYQQQQQSELQ

PPAPSEDIWKKFELLPTPPLSPSRRSGLCSPSYVAVTPFSLRGDNDGGGG

SFSTADQLEMVTELLGGDMVNQSFICDPDDETFIKNIIIQDCMWSGESAA

AKLVSEKLASYQAARKDSGSPNPARGHSVCSTSSLYLQDLSAAASECIDP

SVVFPYPLNDSSSPKSCASQDSSAFSPSSDSLLSSTESSPQGSPEPLVLH

EETPPTTSSDSEEEQEDEEEIDVVSVEKRQAPGKRSESGSPSAGGHSKPP

HSPLVLKRCHVSTHQHNYAAPPSTRKDYPAAKRVKLDSVRVLRQISNNRK

CTSPRSSDTEENVKRRTHNVLERQRRNELKRSFFALRDQIPELENNEKAP

KVVILKKATAYILSVQAEEQKLISEEDLLRKRREQLKHKLEQLRKGELNS

KLEGKPIPNPLLGLDSTRTGHHHHHH.
```

The fusion protein can be modified during or after synthesis to include one or more functional groups. By way of example but not by way of limitation, the protein can be modified to include one or more of an acetyl, phosphate, acetate, amide, alkyl, and/or methyl group. This list is not intended to be exhaustive, and is exemplary only. In some embodiments, the protein includes at least one acetyl group.

A PTD-MYC fusion polypeptide can be generated by any suitable method known the art, e.g. by recombinant protein expression in a cell, such as a bacterial cell, an insect cell, or mammalian cell. In some embodiments, a PTD-MYC fusion polypeptide is recombinantly produced by microbial fermentation. In some embodiments microbial fermentation is performed in a fermentation volume of from about 1 to about 10,000 liters, for example, a fermentation volume of about 10 to about 1000 liters. The fermentation can utilize any suitable microbial host cell and culture medium. In exemplary embodiments, *E. coli* is utilized as the microbial host cell. In alternative embodiments, other microorganisms can be used, e.g., *S. cerevisiae, P. pastoris, Lactobacilli, Bacilli* and *Aspergilli*. In an exemplary embodiment the microbial host cell is BL-21 Star™ *E. coli* strain (Invitrogen). In an exemplary embodiment the microbial host cell is BLR DE3 *E. coli*. strain.

In some embodiments the host cells are modified to provide tRNAs for rare codons, which are employed to overcome host microbial cell codon bias to improve translation of the expressed proteins. In exemplary embodiments, the host cells (e.g., *E. coli*) transformed with a plasmid, such as pRARE (CamR), which express tRNAs for AGG, AGA, AUA, CUA, CCC, GGA codons. Additional, suitable plasmids or constructs for providing tRNAs for particular codons are known in the art and can be employed in the methods provided.

Integrative or self-replicative vectors can be used for the purpose of introducing the PTD-MYC fusion polypeptide expression cassette into a host cell of choice. In an expression cassette, the coding sequence for the PTD-MYC fusion polypeptide is operably linked to promoter, such as an inducible promoter. Inducible promoters are promoters that initiate increased levels of transcription from DNA under their control in response to some change in culture conditions, e.g., the presence or absence of a nutrient or a change in temperature. In some embodiments, the nucleic acid encoding the PTD-MYC fusion polypeptide is codon optimized for bacterial expression.

Exemplary promoters that are recognized by a variety of potential host cells are well known. These promoters can be operably linked to PTD-MYC fusion polypeptide-encoding DNA by removing the promoter from the source DNA, if present, by restriction enzyme digestion and inserting the isolated promoter sequence into the vector. Promoters suitable for use with microbial hosts include, but are not limited to, the β-lactamase and lactose promoter systems (Chang et al., (1978) *Nature*, 275:617-624; Goeddel et al., (1979) *Nature*, 281: 544), alkaline phosphatase, a tryptophan (trp) promoter system (Goeddel (1980) *Nucleic Acids Res.* 8: 4057; EP 36,776), and hybrid promoters such as the tac promoter (deBoer et al., (1983) *Proc. Natl. Acad. Sci. USA* 80: 21-25). Any promoter for suitable for expression by the selected host cell can be used. Nucleotide sequences for suitable are published, thereby enabling a skilled worker operably to ligate them to DNA encoding PTD-MYC fusion polypeptide (see, e.g., Siebenlist et al., (1980) *Cell* 20: 269) using linkers or adaptors to supply any required restriction sites. In exemplary embodiments, promoters for use in bacterial systems can contain a Shine-Dalgarno (S.D.) sequence operably linked to the coding sequence. In some embodiments, the inducible promoter is the lacZ promoter, which is induced with Isopropyl β-D-1-thiogalactopyranoside (IPTG), as is well-known in the art. Promoters and expression cassettes can also be synthesized de novo using well known techniques for synthesizing DNA sequences of interest. In an exemplary embodiment, the expression vector for expression of the PTD-MYC fusion polypeptides herein is pET101/D-Topo (Invitrogen).

For expression of the PTD-MYC fusion polypeptides, the microbial host containing the expression vector encoding the PTD-MYC fusion polypeptide is typically grown to high density in a fermentation reactor. In some embodiments, the reactor has controlled feeds for glucose. In some embodiments, a fermenter inoculum is first cultured in medium supplemented with antibiotics (e.g., overnight culture). The fermenter inoculum is then used to inoculate the fermenter culture for expression of the protein. At an OD600 of at least about 15, usually at least about 20, at least 25, at least about 30 or higher, of the fermenter culture, expression of the recombinant protein is induced. In exemplary embodiments, where the inducible promoter is the lacZ promoter, IPTG is added to the fermentation medium to induce expression of the PTD-MYC fusion polypeptide. Generally, the IPTG is added to the fermenter culture at an OD600 which represents logarithmic growth phase.

In certain embodiments of the methods provided, induced protein expression is maintained for around about 2 to around about 5 hours post induction, and can be from around about 2 to around about 3 hours post-induction. Longer periods of induction may be undesirable due to degradation of the recombinant protein. The temperature of the reaction mixture during induction is preferably from about 28° C. to about 37° C., usually from about 30° C. to about 37° C. In particular embodiments, induction is at about 37° C.

The PTD-MYC fusion polypeptide is typically expressed as cytosolic inclusion bodies in microbial cells. To harvest inclusion bodies, a cell pellet is collected by centrifugation of the fermentation culture following induction, frozen at −70° C. or below, thawed and resuspended in disruption buffer. The cells are lysed by conventional methods, e.g., sonication, homogenization, etc. The lysate is then resuspended in solubilization buffer, usually in the presence of urea at a concentration effective to solubilize proteins, e.g., from around about 5M, 6M, 7M, 8M, 9M or greater. Resuspension may require mechanically breaking apart the pellet and stirring to achieve homogeneity. In some embodiments, the cell pellet is directly resuspended in urea buffer and mixed until homogenous. In some embodiments, the resuspension/solubilization buffer is 8M Urea, 50 mM Phosphate pH 7.5 and the suspension is passed through a homogenizer.

In some embodiments, the homogenized suspension is sulfonylated. For example, in some embodiments, the homogenized suspension is adjusted to include 200 mM Sodium Sulfite and 10 mM Sodium Tetrathionate. The solution is then mixed at room temperature until homogeneous. The mixed lysate is then mixed for an additional period of time to complete the sulfonylation (e.g., at 2-8° C. for ≥12 hours). The sulfonylated lysate was then centrifuged for an hour. The supernatant containing the sulfonylated PTD-MYC fusion polypeptides is then collected by centrifugation and the cell pellet discarded. The supernatant is then passed through a filter, e.g., 0.22 μm membrane filter to clarify the lysate.

The solubilized protein is then purified. Purification methods may include affinity chromatography, reverse phase chromatography, gel exclusion chromatography, and the like. In some embodiments, affinity chromatography is used. For example, the protein is provided with an epitope tag or histidine 6 tag for convenient purification. In the present methods, exemplary PTD-MYC fusion polypeptide comprise histidine 6 tag for purification using Ni affinity chromatography using Ni-resin.

In exemplary embodiments, the Ni-resin column is equilibrated in a buffer containing urea. In some embodiments, the equilibration buffer is 6M Urea, 50 mM Phosphate, 500 mM NaCl, and 10% Glycerol solution. The sulfonylated and clarified supernatant comprising the PTD-MYC fusion polypeptide is then loaded onto the Ni-resin column. The column is then washed with a wash buffer, e.g., 6M Urea, 50 mM Phosphate, 10% Glycerol, 500 mM NaCl, pH 7.5. The column was then washed with sequential wash buffers with decreasing salt concentration. For example, exemplary subsequent washed can include 6M Urea, 50 mM Phosphate, 10% Glycerol, and 2M NaCl, pH 7.5, followed another wash of 6M Urea, 50 mM Phosphate, 10% Glycerol, 50 mM NaCl, and 30 mM Imidazole, pH 7.5.

Following sequential application of the wash buffers the PTD-MYC fusion polypeptide is eluted from the column by addition of elution buffer, e.g., 6M Urea, 50 mM Phosphate, 10% Glycerol, and 50 mM NaCl, pH 7.5 with a gradient from 100 to 300 mM Imidazole, and collecting fractions. The protein containing fractions to be pooled are then filtered through a 0.22 μm membrane. Assessment of protein yield can be measured using any suitable method, e.g., spectrophotometry at UV wavelength 280.

In some embodiments, one or more additional purification methods can be employed to further purify the isolated PTD-MYC fusion polypeptides. In exemplary embodiments, the pooled fractions from the Ni-Sepharose chromatography step are further purified by anion exchange chromatography using a Q-Sepharose resin. In some embodiments, the pool is prepared for loading onto the Q-Sepharose column by diluting the samples to the conductivity of the Q sepharose buffer (17.52+/−1 mS/cm) with the second wash buffer (e.g., 6M Urea, 50 mM Phosphate, 10% Glycerol, 2M NaCl, pH 7.5) from the Ni Sepharose chromatography step. The diluted pool is then loaded onto the Q-Sepharose column, followed by two chase steps using a chase buffer (e.g., 6M Urea, 50 mM Phosphate, 300 mM NaCl, and 10% Glycerol), with further sequential applications of the chase buffer until the UV trace reaches baseline, indicating that the protein has eluted from the column.

Methods of Treatment

The PTD-MYC fusion polypeptide-modified immune cells are administered for the treatment of a melanoma in a patient. In some embodiments, the patient has a metastatic melanoma. In some embodiments, the patient has received one or more agents for the treatment of the melanoma prior to administration of the PTD-MYC fusion polypeptide-modified immune cells. In some embodiments, the melanoma is a relapsed or refractory melanoma. In some embodiments, the melanoma is a metastatic melanoma. In some embodiments, the melanoma is a superficial spreading melanoma, a nodular melanoma, a lentigo maligna melanoma, or an acral melanoma. In some embodiments, the melanoma is resistant to one or more agents for the treatment of the melanoma.

In some embodiments, administration of the PTD-MYC fusion polypeptide-modified immune cells inhibits growth of a melanoma tumor or reduces the volume of a melanoma tumor. In some embodiments, administration of the PTD-MYC fusion polypeptide-modified immune cells to a subject having a melanoma alleviates one or more symptoms of the melanoma. In some embodiments, administration of the PTD-MYC fusion polypeptide-modified immune cells to a subject having melanoma increases the overall survival of the subject. In some embodiments, administration of the PTD-MYC fusion polypeptide-modified immune cells to a subject having melanoma increases the regression of the melanoma.

The administration of the PTD-MYC fusion polypeptide-modified immune cells (e.g. PTD-MYC fusion polypeptide treated tumor infiltrating lymphocytes) according to the methods provided herein can be carried out in any suitable manner for administering cells to a subject, including but not limited to injection, transfusion, implantation or transplantation. In some embodiments, the PTD-MYC fusion polypeptide-modified immune cells are administered to a patient subcutaneously, intradermally, intratumorally, intranodally, intramedullary, intramuscularly, intrathecally, by intravenous or intralymphatic injection, or intraperitoneally. In some embodiments, the PTD-MYC fusion polypeptide-immune cells are administered into a cavity formed by the resection of tumor tissue (i.e. intracavity delivery) or directly into a tumor prior to resection (i.e. intratumoral delivery). In one embodiment, the MYC-fusion polypeptide-immune cells are administered by intravenous injection.

In addition to the PTD-MYC fusion polypeptide-modified immune cells, compositions for administration can comprise any other agents such as pharmaceutically acceptable carriers, buffers, excipients, adjuvants, additives, antiseptics, filling, stabilizing and/or thickening agents, and/or any components normally found in corresponding products. Selection of suitable ingredients and appropriate manufacturing methods for formulating the compositions for particular routes of administration generally known in the art.

The adoptive cell therapeutic composition comprising PTD-MYC fusion polypeptide-modified immune cells can be in any form, such as solid, semisolid or liquid form, suitable for administration. A formulation can be selected from a group consisting of, but not limited to, solutions, emulsions, suspensions, tablets, pellets and capsules. The compositions are not limited to a certain formulation, instead the composition can be formulated into any known pharmaceutically acceptable formulation. The pharmaceutical compositions may be produced by any conventional processes known in the art.

In some embodiments, the administration of the MYC-fusion polypeptide-modified immune cells comprises administering of $10^4$-$10^{10}$ of the cells per kg body weight, including $10^5$ to $10^6$ cells/kg body weight, including all integer values of cell numbers within those ranges. In some embodiments, the cells are administered with or without a course of lymphodepletion, for example with cyclophosphamide.

The MYC-fusion polypeptide-modified immune cells can be administrated in one or more doses. In one embodiment, the therapeutically effective amount of PTD-MYC fusion polypeptide-modified immune cells are administrated as a single dose. In some embodiments, administering a single dose of the PTD-MYC fusion polypeptide-modified immune cells has a therapeutic effect. In another embodiment, the effective amount of MYC-fusion polypeptide-modified immune cells are administrated as more than one dose over a period time. Timing of administration is within the judgment of managing physician and depends on various factors, including, but not limited to the age, gender, or clinical condition of the patient and characteristics of the melanoma, including type, degree or location of melanoma. While individual needs vary, determination of optimal ranges of effective amounts of a MYC-fusion polypeptide-modified immune cell for treatment of a particular disease or conditions are within the skill of one in the art.

PTD-MYC fusion polypeptide-modified immune cells can be administered for example from 1 to 10 times in the first 2 weeks, 3 weeks, 4 weeks, monthly or during the treatment period. In some embodiments, PTD-MYC fusion polypeptide-modified immune cells are administered 2, 3, 4, 5, 6, 7, 8, 9, or 10 times. In some embodiments, PTD-MYC fusion polypeptide-modified immune cells are administered weekly, every 2 weeks, every 3 weeks or monthly.

A therapeutically effective amount means an amount which provides a therapeutic or prophylactic benefit. The dosage administrated will be dependent upon the age, health and weight of the recipient, kind of concurrent treatment, if any, frequency of treatment and the nature of the effect desired.

In some embodiments, a patient receiving PTD-MYC modified immune cells are first pretreated with one or more cytokines and/or other immunomodulatory agents. In some embodiments, a patient receiving PTD-MYC modified immune cells is lymphodepleted prior to administration of the PTD-MYC modified immune cells. The purpose of lymphodepletion is to make room for the infused lymphocytes, in particular by eliminating regulatory T cells and other non-specific T cells which compete for homeostatic cytokines.

In some embodiments, the PTD-MYC modified immune cells are administered with an additional therapeutic agent. In some embodiments, additional therapeutic agent is administered prior to, simultaneously with, intermittently with, or following treatment with the PTD-MYC modified immune cells. In some embodiments, the additional therapeutic agent is an immunomodulator, such as an interleukin (e.g. IL-2, IL-7, IL-12), a cytokine, a chemokine, or and immunomodulatory drug. In some embodiments, the cytokine is selected from among cytokine is selected from a group consisting of interferon alpha, interferon beta, interferon gamma, complement C5a, IL-2, TNFα, CD40L, IL12, IL-23, IL15, IL17, CCL1, CCL11, CCL12, CCL13, CCL14-1, CCL14-2, CCL14-3, CCL15-1, CCL15-2, CCL16, CCL17, CCL18, CCL19, CCL19, CCL2, CCL20, CCL21, CCL22, CCL23-1, CCL23-2, CCL24, CCL25-1, CCL25-2, CCL26, CCL27, CCL28, CCL3, CCL3L1, CCL4, CCL4L1, CCL5 (=RANTES), CCL6, CCL7, CCL8, CCL9, CCR10, CCR2, CCR5, CCR6, CCR7, CCR8, CCRL1, CCRL2, CX3CL1, CX3CR, CXCL1, CXCL10, CXCL11, CXCL12, CXCL13, CXCL14, CXCL15, CXCL16, CXCL2, CXCL3, CXCL4, CXCL5, CXCL6, CXCL7, CXCL8, CXCL9, CXCL9, CXCR1, CXCR2, CXCR4, CXCR5, CXCR6, CXCR7 and XCL2. In some embodiments, the additional therapeutic agent is an anticancer agent, such as chemotherapy or radiation therapy.

In some embodiments, the modified immune cells administered for the treatment of melanoma are T cells with genetically modified antigen receptors, including chimeric antigen receptor (CAR)-T cells. Various strategies can, for example, be employed to genetically modify T cells by altering the specificity of the T cell receptor (TCR), for example, by introducing new TCR α and β chains with selected peptide specificity (see, e.g., U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088,379). Chimeric antigen receptors (CARs) can be used in order to generate immunoresponsive cells, such as T cells, specific for selected targets, such as malignant cells, with a wide variety of receptor chimera constructs having been described (see, e.g. U.S. Pat. Nos. 5,843,728; 5,851,828; 5,912,170; 6,004,811; 6,284,240; 6,392,013; 6,410,014; 6,753,162; 8,211,422; and, PCT Publication WO9215322). Methods for the preparation of CART cells are known in the art and can be used in combination with the methods provided herein to generate modified CAR T cells comprising a MYC fusion polypeptide (e.g. PTD) as described herein.

In general, CARs are comprised of an extracellular domain, a transmembrane domain, and an intracellular domain, wherein the extracellular domain comprises an antigen-binding domain that is specific for a predetermined target. While the antigen-binding domain of a CAR is often an antibody or antibody fragment (e.g., a single chain variable fragment, scFv), the binding domain is not particularly limited so long as it results in specific recognition of a target. For example, in some embodiments, the antigen-binding domain may comprise a receptor, such that the CAR is capable of binding to the ligand of the receptor. Alternatively, the antigen-binding domain may comprise a ligand, such that the CAR is capable of binding the endogenous receptor of that ligand.

In some embodiments, the T cells expressing a desired CAR are selected through co-culture with γ-irradiated activating and propagating cells (AaPC), which co-express the melanoma antigen and co-stimulatory molecules. In some embodiments, the engineered CAR T-cells are expanded, for example by co-culture on AaPC in presence of soluble factors, such as IL-2 and IL-21. This expansion can for example be carried out so as to provide memory CAR+ T cells. In this way, CAR T cells can be provided that have specific cytotoxic activity against antigen-bearing tumors (optionally in conjunction with production of desired chemokines such as interferon-γ).

In some embodiments, the CAR T-cells are contacted with a PTD-MYC fusion polypeptide provided herein in vitro to generation a modified CAR T cells for the treatment of a melanoma. The modified CAR T cells can be administered according any suitable method, including the methods for administration of the PTD-MYC fusion polypeptide-modified immune cells as described above.

Kits

Pharmaceutical compositions comprising MYC-fusion polypeptides and/or MYC-fusion polypeptide-modified immune cells provided herein can be assembled into kits or pharmaceutical systems for use in treating a melanoma. Kits according to this embodiment can comprise a carrier means, such as a box, carton, tube, having in close confinement therein one or more containers, such as vials, tubes, ampoules, bottles, syringes, or bags. The kits can also comprise associated instructions for using the MYC-fusion polypeptides and/or MYC-fusion polypeptide-modified immune cells.

In some embodiments, the kit comprises an effective amount of an adoptive cell therapy, such as MYC-fusion polypeptide-modified immune cells. In some embodiments, the kit comprises one for more reagents for the detection of the administered MYC-fusion polypeptides and/or MYC-fusion polypeptide-modified immune cells. In some embodiments, the kit comprises cells for treatment with a MYC-fusion polypeptide provided herein, for example, hematopoietic stem cells, donor leukocytes, T cells, or NK cells. In some embodiments, the kit further comprises an effective amount of a therapeutic agent to be administered in combination with MYC-fusion polypeptides and/or MYC-fusion polypeptide-modified immune cells provided herein. In some embodiments, therapeutic agent is an anti-cancer agent.

Kits provided herein also can include a device for administering MYC-fusion polypeptides and/or MYC-fusion polypeptide-modified immune cells provided herein to a subject. Any of a variety of devices known in the art for administering polypeptides and cells to a subject can be included in the kits provided herein. Exemplary devices include a hypodermic needle, an intravenous needle, a catheter, a needle-less injection, but are not limited to, a hypodermic needle, an intravenous needle, a catheter, a needle-less injection device, an inhaler and a liquid dispenser such as an eyedropper. Typically the device for administering the MYC-fusion polypeptides and/or MYC-fusion polypeptide-modified immune cells of the kit will be compatible with the desired method of administration of the composition. For example, a composition to be delivered intravenously can be included in a kit with a hypodermic needle and a syringe.

EXAMPLES

Example 1. Immune Cells Treated with TAT-MYC to Generate TAT-MYC-Treated Lymphocytes for Immunotherapy of Melanoma Tumors In this example, the ability of a PTD-MYC fusion polypeptide comprising the protein transduction domain of HIV-1 transactivation protein (TAT) and MYC to modulate an immune response against melanoma cells in vivo was examined. Specifically, the ability of lymphoid cells, derived from melanoma-bearing mice and treated with TAT-MYC, to treat mice harboring melanoma tumors was studied. The object of these studies was to determine whether immune cells derived from melanoma bearing mice and treated with TAT-MYC to generate TAT-MYC lymphocytes would be an effective treatment for melanoma tumors upon transplantation into melanoma bearing mice.

Materials and Methods

C57BL/6J is the most widely used inbred strain and the first to have its genome sequenced. Although this strain is refractory to many tumors, it is a permissive background for maximal expression of most mutations. C57BL/6J mice are resistant to audiogenic seizures, have a relatively low bone density, and develop age-related hearing loss. They are also susceptible to diet-induced obesity, type 2 diabetes, and atherosclerosis. Macrophages from this strain are resistant to the effects of anthrax lethal toxin.

Treatment Groups

Fifteen C57BL/6 mice (Jackson Laboratory Stock #000664) weighing approximately 25 g and harboring melanoma tumors were generated and divided into 3 cohorts of 5 animals, one cohort of one mouse as a no treatment control, one cohort treated with Lymphoid cells derived from tumor-bearing mice and treated with control TAT-fusion protein, and one cohort treated with TAT-MYC lymphocytes.

Generation of Tumor-Bearing Donor Mice and Preparation of Donor Cells

B16-F10 melanoma cells (ATCC CRL 6475, mouse skin melanoma) for implantation were cultured in D10 media (DMEM, 10% FBS, Pen/Strep (10,000 units per/ml) (Gibco Cat #15140); L-glutamine (200 mM) (Gibco Cat #25030); MEM Non-essential Amino Acids (Gibco Cat #11140)).

The C57BL/6j mice (Jackson Laboratory #003548) were implanted with $1\times10^4$ B16-F10 melanoma cells in 250 µL PBS via tail vein injection. Prior to injection, each test mouse was placed under a 250 W heat lamp for 1-2 minutes and then injected intravenously with the melanoma cells. At 14 days post-transplant, lymph nodes from the injected mice were harvested and ground with the plunger of a 10 mL syringe.

For the first study, lymph nodes were harvested from 5 mice. For the second lymph nodes were harvested from 10 mice. The cells were washed with C10, collected and spun at 260×g for 5 min. After discarding the supernatant, the cells were resuspended in 10 mL sterile TAC, spun at 260×g for 5 minutes. After discarding the supernatant, the cells were resuspended in 2 mL of sterile filtered PBS with 5% BSA.

The lymph node cells were treated with TAT-MYC to generate TAT-MYC lymphocytes or treated with a control TAT-Fusion protein. The cells were split into 2, 15 mL conical tubes (1 mL each), treated with 1 mL of 25 ug/ml of a control protein (TAT-CRE for experiment 1, TAT-GFP for experiment 2) or 1 mL of 25 ug/ml of TAT-MYC lot C18. After one hour of room temp incubation, each tube was washed with sterile PBS three times, transferred to 5 mL sterile tubes and placed on ice.

The test mice were prepared by injecting $1\times10^4$ B16-F10 melanoma cells in 250 uL PBS into the tail vein for each cohort of 5 C57BL/6j mice. After injection, the mice were observed once daily. Changes in body weight, food consumption, activity, and mortality were monitored. At 7 days post-transplant, TAT-MYC lymphocytes or control lymphoid cells were then transplanted into melanoma cell injected mice.

Symptoms were monitored daily. The mice were euthanized when severe symptoms presented and deaths were recorded. Mice were either found dead or euthanized if found with severe symptoms such as heavy breathing, hunched back and immobility. Day of death was recorded with day of treatment as Day 0.

Figure 2:
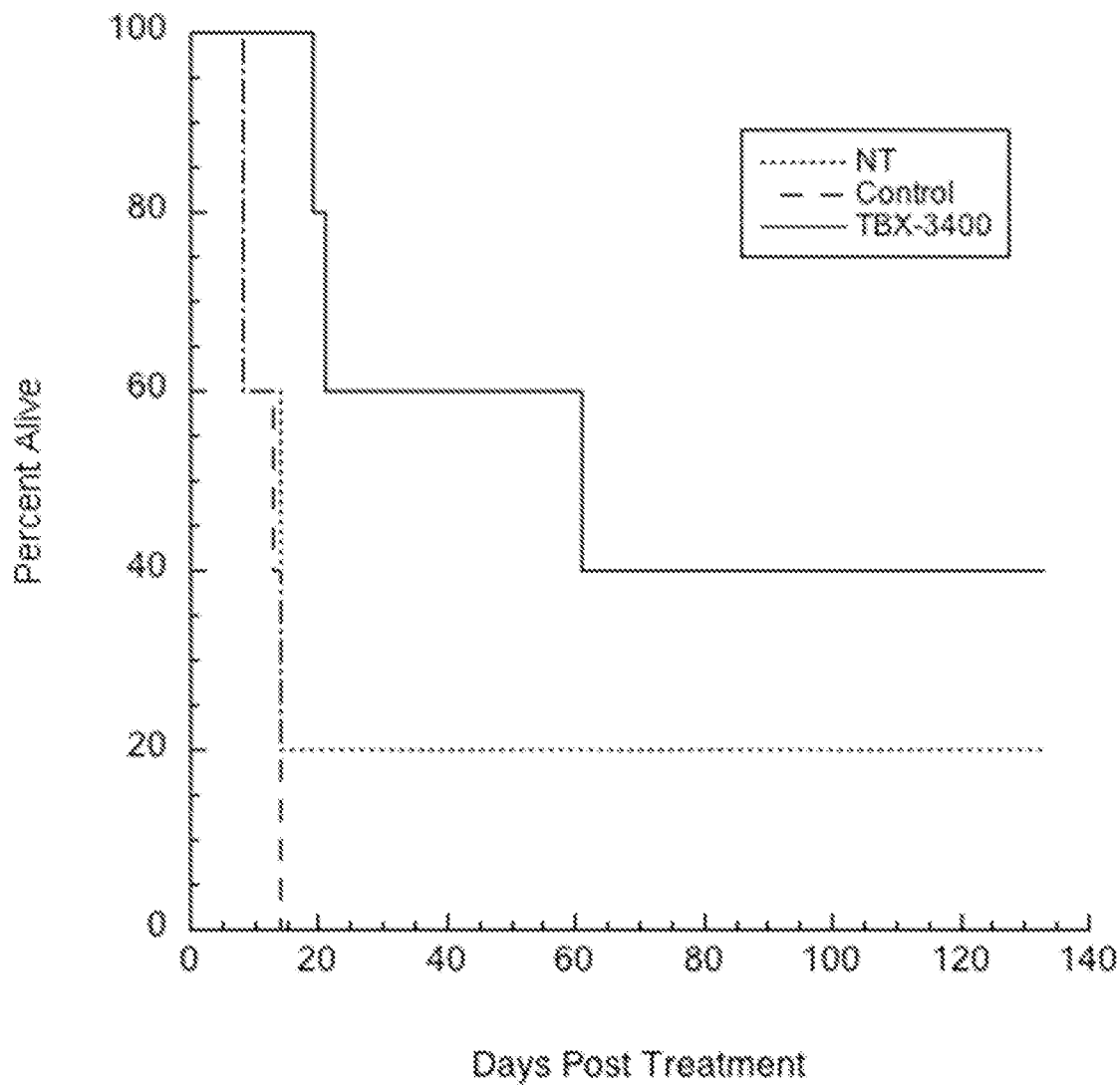
FIG. 2 illustrates results for survival of melanoma tumor-bearing mice following infusion of lymphocytes from tumor-bearing donor mice treated with TAT-MYC (repeat of experiment shown in FIG. 1). Mice were treated with TAT-MYC lymphocytes, lymph cells treated with a control protein or left untreated. Day of death recorded with day of treatment as Day 0.

The results from Experiments 1 and 2 are shown in FIGS. 1 and 2, respectively. As shown in the figures, treating melanoma-bearing mice with TAT-MYC lymphocytes (TBX-3400) generated by contacting mouse lymphoid cells derived from melanoma bearing mice with TAT-MYC, significantly improved the overall survival of the mice compared to transplanting lymphoid cells treated with control TAT-Fusion protein. These results suggest that TAT-MYC treatment of immune cells are useful in the treatment of melanoma using adoptive cell transfer.

Figure 3:
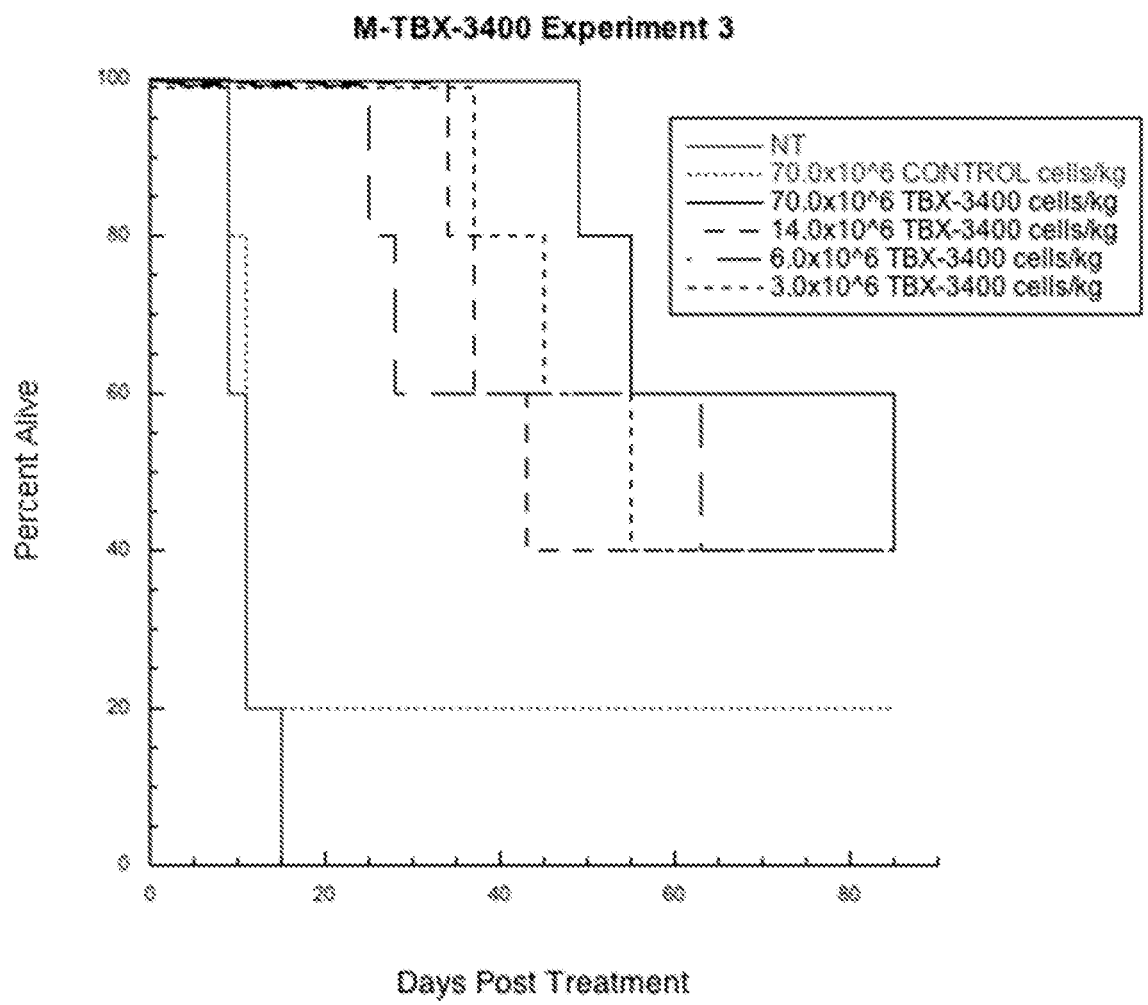
FIG. 3 illustrates results for survival of melanoma tumor-bearing mice following infusion of different amounts of lymphocytes from tumor-bearing donor mice treated with TAT-MYC. Mice were treated with TAT-MYC lymphocytes, lymph cells treated with a control protein or left untreated. Day of death recorded with day of treatment as Day 0.
Figure 4:
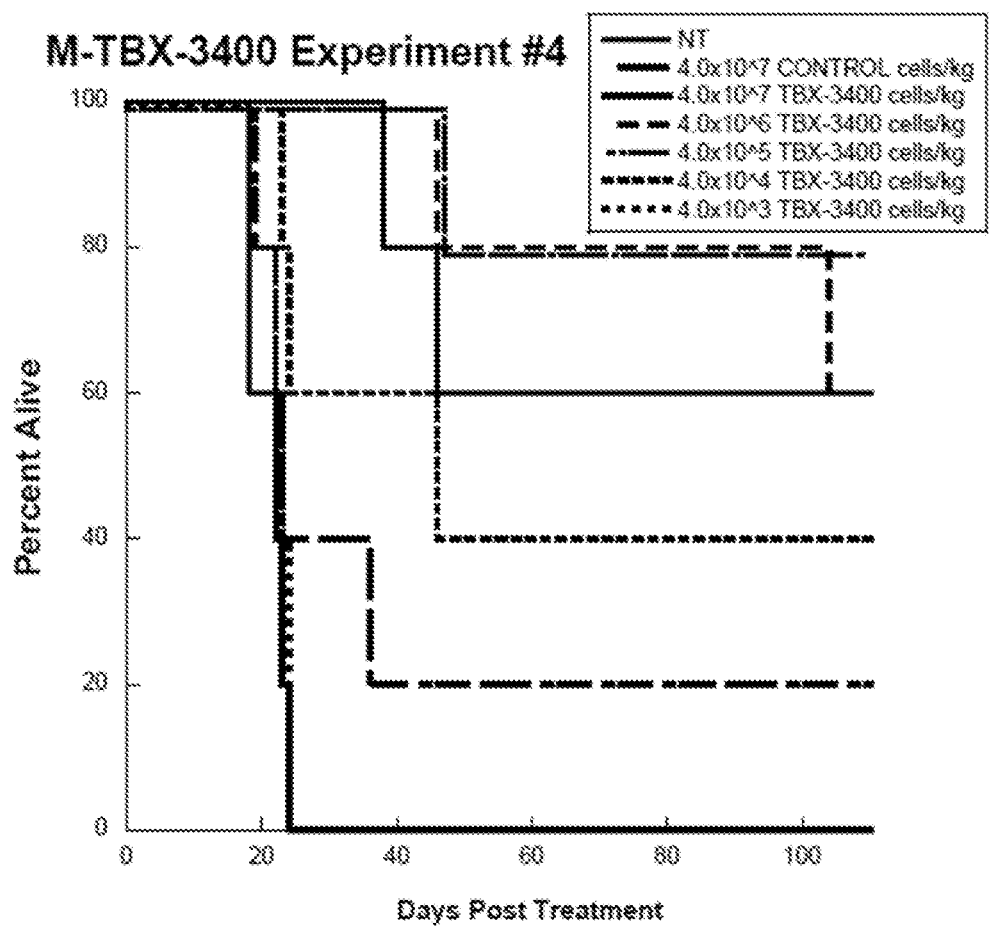
FIG. 4 illustrates results for survival of melanoma tumor-bearing mice following infusion of different amounts of lymphocytes from tumor-bearing donor mice treated with TAT-MYC. Mice were treated with TAT-MYC lymphocytes, lymph cells treated with a control protein or left untreated. Day of death recorded with day of treatment as Day 0.

Example 2. Dose Response Effect of TAT-MYC-Treated Lymphocytes for Immunotherapy of Melanoma Tumors In this example, the therapeutic effects of different amounts administered TAT-MYC-treated lymphocytes for immunotherapy of melanoma tumors was examined. This experiment was performed as described above in Example 1, except that several different doses of the TAT-MYC-treated lymphocytes were injected and compared. Two experiments were performed. In the first experiment, Experiment 3, TAT-MYC lymphocytes were administered to the melanoma-bearing mice via tail vein injection according to the following dosing groups: $3.0\times10^6$ cells/kg, $6.0\times10^6$ cells/kg, $14.0\times10^6$ cells/kg, and $70.0\times10^6$ cells/kg. For the control groups, the mice were administered $70.0\times10^6$ TAT-Cre treated or no cells (NT). In the second experiment, Experiment 4, TAT-MYC lymphocytes were administered to the melanoma-bearing mice via tail vein injection according to the following dosing groups: $4.0\times10^3$ cells/kg, $4.0\times10^4$ cells/ kg, $4.0×10^5$ cells/kg, $4.0×10^6$ cells/kg and $4.0×10^7$ cells/kg. For the control groups, the mice were administered $4.0×10^6$ TAT-Cre treated or no cells (NT). The results from Experiments 3 and 4 are shown in FIGS. 3 and 4, respectively. As shown in the figures, treating melanoma-bearing mice with increasing amounts of TAT-MYC lymphocytes (TBX-3400) led to a significantly improved overall survival rate in both experiments. These experiments demonstrate the both the reproducibility and efficacy of TAT-MYC lymphocytes for treating melanoma-bearing subjects.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

---

What is claimed is:

1. A composition comprising:
   (a) a MYC fusion peptide, comprising (i) a protein transduction domain; (ii) a MYC polypeptide sequence, wherein the MYC fusion peptide comprises SEQ ID NO: 1; and
   (b) one or more primary immune cells from a donor subject that has a melanoma tumor, wherein the one or more primary immune cells are reactive against a melanoma-specific antigen.

2. The composition of claim 1, wherein the protein transduction domain sequence is a TAT protein transduction domain sequence.

3. The composition of claim 1, wherein the one or more immune cells comprises a T cell, a B cell, an NK cell, or any combination thereof.

4. The composition of claim 1, wherein the one or more immune cells comprises a tumor-infiltrating lymphocyte, T-cell receptor modified lymphocyte, or a chimeric antigen receptor modified lymphocyte.

5. The composition of claim 4, wherein the tumor-infiltrating lymphocyte has a CD8+CD25+ signature or a CD4+CD25+ signature.

* * * * *